(12) United States Patent
Heeney et al.

(10) Patent No.: US 7,183,418 B2
(45) Date of Patent: Feb. 27, 2007

(54) MONO-, OLIGO- AND POLYTHIENO[2,3-B]THIOPHENES

(75) Inventors: Martin Heeney, Southampton (GB); Iain McCulloch, Southampton (GB); Clare Bailey, Southampton (GB)

(73) Assignee: Merck Patent Gesellschaft, Darmstadt (DE)

( * ) Notice: Subject to any disclaimer, the term of this patent is extended or adjusted under 35 U.S.C. 154(b) by 354 days.

(21) Appl. No.: 10/928,724

(22) Filed: Aug. 30, 2004

(65) Prior Publication Data
US 2005/0090640 A1   Apr. 28, 2005

(30) Foreign Application Priority Data
Aug. 28, 2003   (EP) ................... 03019501

(51) Int. Cl.
C07D 495/02    (2006.01)
H01B 1/00      (2006.01)
C08G 75/00     (2006.01)
G02B 6/00      (2006.01)
G02F 1/35      (2006.01)

(52) U.S. Cl. ............... 549/50; 252/500; 528/377; 385/143; 359/326

(58) Field of Classification Search ........... 549/50; 252/500; 528/377; 385/143; 359/326
See application file for complete search history.

(56) References Cited

U.S. PATENT DOCUMENTS 4,639,328 A   1/1987   Krause et al.
5,684,165 A * 11/1997  Cabrera et al. ............ 549/50
6,130,339 A * 10/2000  Tan et al. ................. 549/50
6,800,763 B2* 10/2004  Farrand et al. ............ 549/50
7,118,692 B2* 10/2006  Nordquist et al. ......... 252/500

FOREIGN PATENT DOCUMENTS

EP   0144013   6/1985
EP   1275651   1/2003
EP   1300430   4/2003

OTHER PUBLICATIONS

Kossmehl et al., "Synthesen und charakterisierung von Poly(thieno[2,3-b]thiophen-2,5-diylvinylenarylenvinylen)en, Poly(thienol[3,2-b]thiophen-2,5-diylvinylenarylenvinylen)en und einigen Modellverbindungen," Makromol. Chem, 1982, pp. 2747-2769, vol. 183.

Kossmehl et al., "über Polyarylenalkenylene und polyheteroarylenalkenylene, 12 Synthesen und Charakterisierung von Poly(thieno'2,3-b!thiophen-2,5-diylvinylen arylenvinylen)en, Poly(thieno'2,3-b! thiophen-2,5-diylvinylenarylenvinylen)en, und einigen modellverbindungen," Makromol. Chem., 1982, pp. 2747-2769, vol. 183, XP002305732; pp. 2748; table 6.

* cited by examiner

Primary Examiner—Deborah C. Lambkin

(57) ABSTRACT

The invention relates to novel mono-, oligo and poly[2,3-b]-thienothiophenes, their use as semiconductors or charge transport materials, in optical, electro-optical or electronic devices like for example liquid crystal displays, optical films, organic field effect transistors (FET or OFET) for thin film transistor liquid crystal displays and integrated circuit devices such as RFID tags, electroluminescent devices in flat panel displays, and in photovoltaic and sensor devices, and to a field effect transistor, light emitting device or ID tag comprising the novel polymers.

20 Claims, 4 Drawing Sheets

MONO-, OLIGO- AND POLYTHIENO[2,3-B]THIOPHENES

FIELD OF INVENTION

The invention in one aspect relates to novel mono-, oligo- and polythieno[2,3-b]thiophenes, and to their use as semiconductors or charge transport materials, in optical, electrooptical or electronic devices like for example liquid crystal displays, optical films, organic field effect transistors (FET or OFET) for thin film transistor liquid crystal displays and integrated circuit devices such as RFID tags, electroluminescent devices in flat panel displays, and in photovoltaic and sensor devices. The invention in other aspects further relates to a field effect transistor, light emitting device or ID tag comprising the novel polymers.

BACKGROUND AND PRIOR ART

Organic materials have recently shown promise as the active layer in organic based thin film transistors and organic field effect transistors [see H. E. Katz, Z. Bao and S. L. Gilat, *Acc. Chem. Res.*, 2001, 34, 5, 359]. Such devices have potential applications in smart cards, security tags and the switching element in flat panel displays. Organic materials are envisaged to have substantial cost advantages over their silicon analogues if they can be deposited from solution, as this enables a fast, large-area fabrication route.

The performance of the device is principally based upon the charge carrier mobility of the semi-conducting material and the current on/off ratio, so the ideal semiconductor should have a low conductivity in the off state, combined with a high charge carrier mobility ($>1 \times 10^{-3}$ cm$^2$ V$^{-1}$ s$^{-1}$). In addition, it is important that the semi-conducting material is relatively stable to oxidation i.e. it has a high ionisation potential, as oxidation leads to reduced device performance.

Regioregular head-to-tail poly(3-hexylthiophene) has been reported with charge carrier mobility between $1 \times 10^{-5}$ and $4.5 \times 10^{-2}$ cm$^2$ V$^{-1}$ s$^{-1}$, but with a rather low current on/off ratio between 10 and $10^3$ [see Z. Bao et al., *Appl. Pys. Lett.*, 1996, 69, 4108]. This low on/off current is due in part to the low ionisation potential of the polymer, which can lead to oxygen doping of the polymer under ambient conditions, and a subsequent high off current [see H. Sirringhaus et al., *Adv. Solid State Phys.*, 1999, 39, 101].

A high regioregularity leads to improved packing and optimised microstructure, leading to improved charge carrier mobility [see H. Sirringhaus et al., *Science*, 1998, 280, 1741–1744; H. Sirringhaus et al., *Nature*, 1999, 401, 685–688; and H. Sirringhaus, et al., *Synthetic Metals*, 2000, 111–112, 129–132]. In general, poly(3-alkylthiophenes) show improved solubility and are able to be solution processed to fabricate large area films. However, poly(3-alkylthiophenes) have relatively low ionisation potentials and are susceptible to doping in air.

It is an aim of the present invention to provide new materials for use as semiconductors or charge transport materials, which are easy to synthesize, have high charge mobility, good processibility and oxidative stability.

Another aim of the invention is to provide new semiconductor and charge transport components, and new and improved electrooptical, electronic and electroluminescent devices comprising these components, like field effect transistors (FET) as components of integrated circuitry or of thin film transistors (TFT), and organic light emitting diode (OLED) applications like electroluminescent displays or backlights of liquid crystal displays.

Other aims of the invention are immediately evident to those skilled in the art from the following description.

The inventors have found that these aims can be achieved by providing mono-, oligo- and (co)polymers of thieno[2,3-b]thiophene as semiconductors and charge transport materials.

The inventors of this invention have found that incorporation of thieno[2,3-b]thiophene (1) units into conjugated polymers yields materials which are useful for charge transport in FET's, and for electroluminescence in OLED's. The incorporation of this core has the effect of lowering the ionisation potential of the resulting polymers, resulting in improved air stability and reduced transistor off currents. It is believed that this effect is due to the fact that quinoidal type resonance structures cannot be formed for thieno[2,3-b]thiophene as shown in Diagram 1, which therefore limits the effective conjugation length of the polymer backbone, since charge cannot delocalise through this unit. This is in contrast for the other regioisomer, thieno[3,2-b]thiophene (2), or 2,2-bithiophene (3), in which fully delocalised quinoidal-type structures can be realised, as shown in Diagram 1.

Diagram 1: Charge delocalisation though dithiophene units, where A represents a conjugated species such as a thiophene or benzene ring.

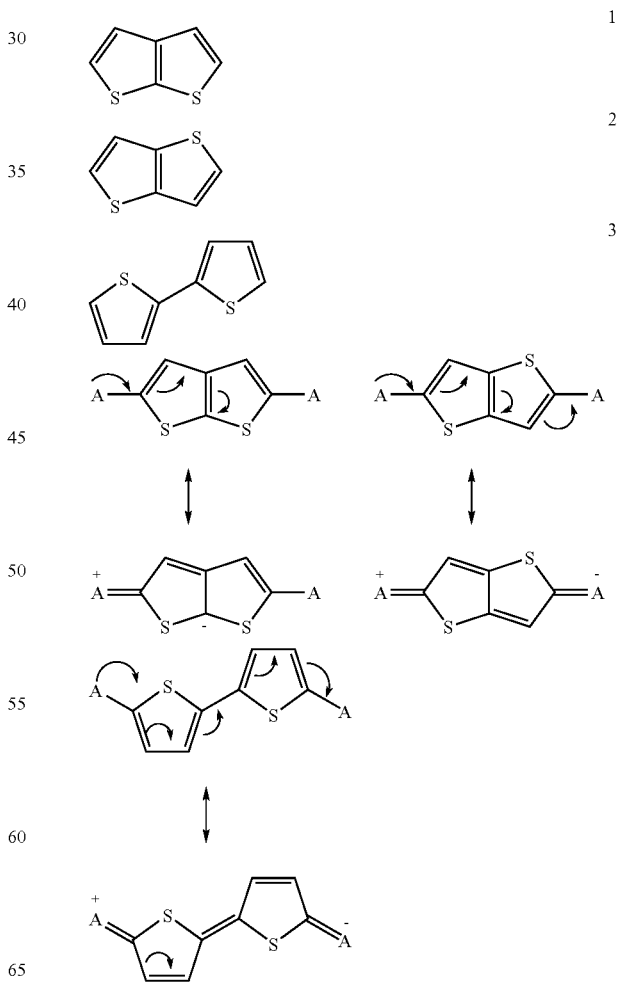

Therefore once an exciton or hole is formed in the polymer, it cannot fully delocalise along the polymer backbone, as depicted in Diagram 2. This limits the effective conjugation to only the aromatic units between any two thieno[2,3-b]thiophenes (in Diagram 2, effectively 2 thiophene units plus 2 thieno[2,3-b]thiophene units). This provides a ready means to tune the effective conjugation length in a conjugated polymer. This is desirable because shorter conjugation lengths result in lower HOMO energy levels (since there are less degenerate states) and therefore improved oxidative stability. Since the dominant mechanism for charge transport in conjugated polymers is via a hole-hopping mechanism, the polymers are still able to exhibit good mobilities providing close packed morphology is obtained.

Diagram 2: Effective conjugation in a co-polymer containing thieno[2,3-b]thiophene.

G. Koβmehl et al., Makromol. Chem. 1982, 183, 2747–2769 disclose poly(thieno[2,3-b]thiophene-2,5-divinylenearylene), wherein the arylene group is 2,5-thiophene, 1,4-phenylene or 2,5-dimethoxy-1,4-phenylene. However, copolymers of this type with a vinyl linker do often show stability problems, and copolymers comprising unsubstituted or methoxy substituted phenylene groups often have low solubility.

SUMMARY OF THE INVENTION

The invention relates to mono-, oligo- and polymers, characterized in that they are compounds of formula I $$—[(A)_a—(B)_b—(C)_c—(D)_d]_n—$$  I wherein

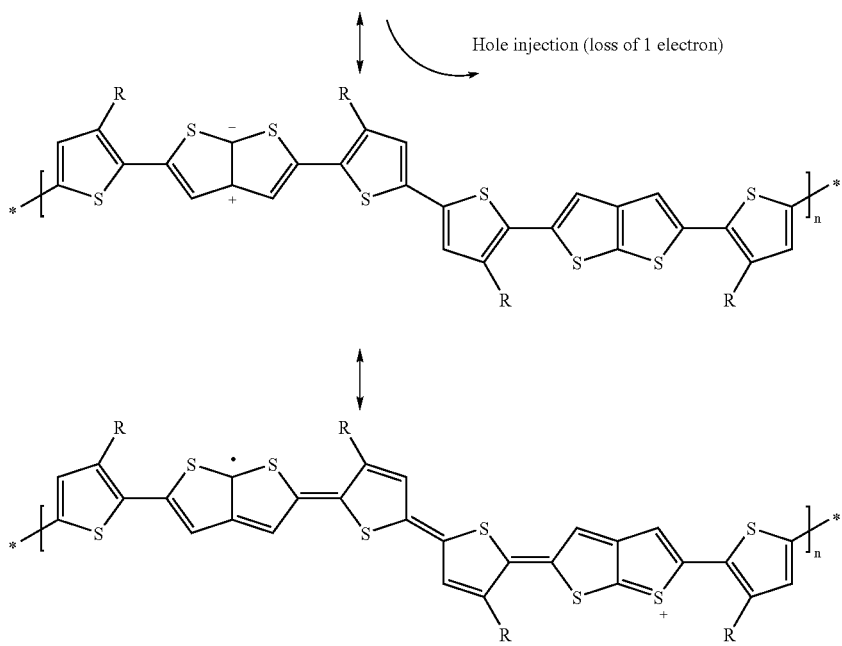

Effective conjugation

Hole injection (loss of 1 electron)

In electroluminescent applications this provides a ready means to colour tune the polymers, and also results in improved colour purity since each polymer chain now has the same effective conjugation length.

Furthermore, in contrast to other aromatic units that cannot form quinoidal type delocalisation, such as meta-substituted benzenes, or 2,7-substituted naphthalene's, thieno[2,3-b]thiophene has a linear shape and does not introduce 'kinks' in the polymer backbone. Such 'kinks' can result in amorphous polymers.

A and C denote independently of each other, and each of A and C in case of multiple occurrence independently of one another, a group of formula II

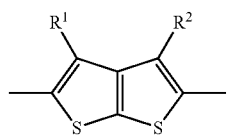

II

R¹ and R² are independently of each other H, halogen or straight chain, branched or cyclic alkyl with 1 to 20 C-atoms, which may be unsubstituted, mono- or poly-substituted by F, Cl, Br, I, OH or CN, it being also possible for one or more non-adjacent $CH_2$ groups to be replaced, in each case independently from one another, by —O—, —S—, —NH—, —NR⁰—, —SiR⁰R⁰⁰—, —CO—, —COO—, —OCO—, —OCO—O—, —S—CO—, —CO—S—, —CH=CH— or —C≡C— in such a manner that O and/or S atoms are not linked directly to one another, or denotes optionally substituted aryl or heteroaryl, P—Sp— or P*—Sp—, P is a polymerisable or reactive group, P* is a group that can be converted to or substituted by a polymerisable or reactive group P, Sp is a spacer group or a, single bond, R⁰ and R⁰⁰ are independently of each other H, aryl or alkyl with 1 to 12 C-atoms, B and D are independently of each other, and each of B and D in case of multiple occurrence independently of one another, —CX¹=CX²—, —C≡C— or an arylene or heteroarylene group that is optionally substituted with one or more groups R¹, X¹ and X² are independently of each other H, F, Cl or CN, a, b, c, d are independently of each other 0 or an integer from 1 to 10, with a+b+c+d>0, and wherein in at least one recurring unit $[(A)_a—(B)_b—(C)_c—(D)_d]$ at least one of a and c is 1 and at least one of b and d is 1, and n is an integer ≧1, wherein the recurring units $[(A)_a—(B)_b—(C)_c—(D)_d]$ can be identical or different, and with the proviso that if a is 1, then $—(B)_b—(C)_c—(D)_d—$ is different from —CH=CH—Ar—CH=CH—, with Ar being 2,5-thiophene, 1,4-phenylene or 2,5-dimethoxy-1 4-phenylene, or the compounds comprise at least one group P—Sp—or P*—Sp—.

The invention further relates to a semiconductor or charge transport material, component or device comprising at least one mono-, oligo- or polymer as defined above.

The invention further relates to the use of polymers according to the invention as semiconductors or charge transport materials, in particular in optical, electrooptical or electronic devices, like for example in field effect transistors (FET) as components of integrated circuitry, as thin film transistors in flat panel display applications or for Radio Frequency Identification (RFID) tags, or in semiconducting components for organic light emitting diode (OLED) applications such as electroluminescent displays or backlights of e.g. liquid crystal displays (LCD), for photovoltaic or sensor devices, as electrode materials in batteries, as photoconductors and for electrophotographic applications like electrophotographic recording.

The invention further relates to the use of the novel mono-, oligo- and polymers according to the present invention as electroluminescent materials, in photovoltaic or sensor devices, as electrode materials in batteries, as photoconductors, for electrophotographic applications like electrophotographic recording and as alignment layer in LCD or OLED devices.

The invention further relates to an optical, electrooptical or electronic device, FET, integrated circuit (IC), TFT, OLED or alignment layer comprising a semiconducting or charge transport material, component or device according to the invention.

The invention further relates to a TFT or TFT array for flat panel displays, radio frequency identification (RFID) tag, electroluminescent display or backlight comprising a semiconducting or charge transport material, component or device or a FET, IC, TFT or OLED according to the invention.

The invention further relates to a security marking or device comprising a FET or an RFID tag according to the invention.

DETAILED DESCRIPTION OF THE INVENTION

Figure 1:
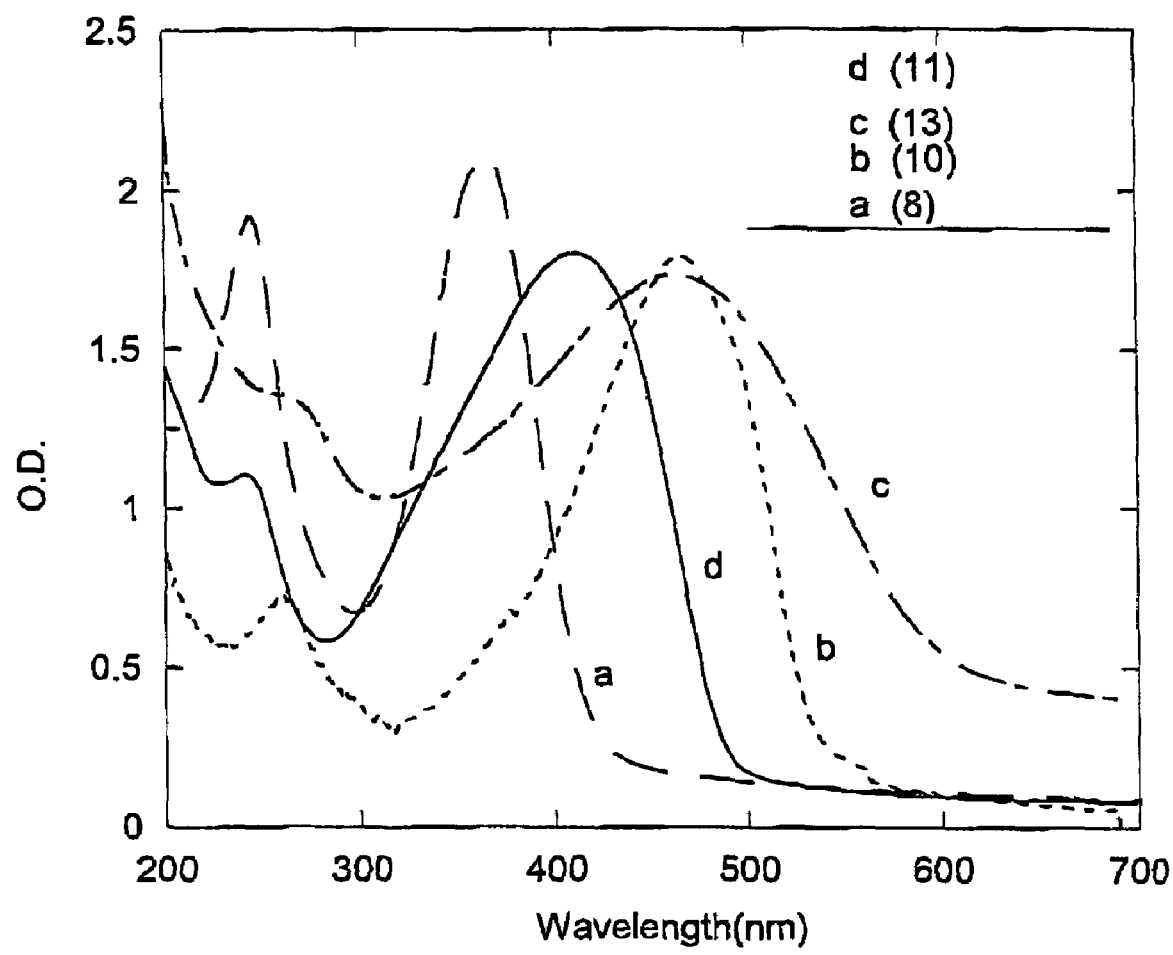
FIG. 1 shows the UV spectra of polymers according to the present invention.

The mono-, oligo and polymers according to the invention are especially useful as charge transport semiconductors in that they have high carrier mobilities. Particularly preferred are polymers wherein the thieno[2,3-b]thiophene group is unsubstituted or substituted by one or more alkyl groups. The introduction of alkyl side chains into the thienothiophene group improves their solubility and therefore their solution processibility.

Copolymerisation of the thieno[2,3-b]thiophene core with functionalised aromatic or unsaturated comonomers can further improve the solubility and the charge transport properties. Variation of the aromatic comonomers provides a method of tailoring the band gap of the polymers. This will lead to better stability and higher charge carrier mobility.

Particularly preferred are mono-, oligo-, and polymers of formula I1

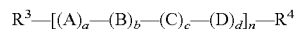
$$R^3—[(A)_a—(B)_b—(C)_c—(D)_d]_n—R^4 \qquad \text{I1}$$

wherein A, B, C, D, a, b, c and d have independently-of each other one of the meanings of formula I, and R³ and R⁴ are independently of each other H, halogen, Sn(R⁰)₃, B(OR⁰)₂ CH₂Cl, COH, CH=CH₂, SiR⁰R⁰⁰R⁰⁰⁰, optionally substituted aryl or heteroaryl, P—Sp—or P*—Sp—, with P, P*, Sp, R⁰ and R⁰⁰ having the meanings of formula I and R⁰⁰⁰ having one of the meanings of R⁰⁰ in formula I.

In the oligo- and polymers of the present invention the recurring units $[(A)_a-(B)_b—(C)_c-(D)_d]$ in case of multiple occurrence can be selected of formula I independently of each other, so that an oligo- or polymer may comprise identical or different recurring units $[(A)_a—(B)_b—(C)_c—(D)_d]$. The oligo- and polymers thus include homopolymers and copolymers like for example statistically random copolymers, for example with a monomer sequence such as —A—B—C—C—B—D—A—B—D— or —A—C—A—A—C—, alternating copolymers, for example with a monomer sequence such as —A—B—C—D—A—B—C—D— or —A—B—C—A—B—C—, and block copolymers, for example with a monomer sequence such as —A—A—B—B—B—B—C—C—C—D—D—D—, wherein the groups A, B, C and D preferably together form a conjugated system, and wherein multiple groups (for example each group B in the sequence —B—B—B—B—) can be identical or different from one another.

Especially preferred are mono-, oligo- and polymers comprising one or more recurring units [(A)$_a$—(B)$_b$—(C)$_c$—(D)$_d$], wherein a is 1, c is 0 and b or d is an integer from 1 to 10, preferably 1, 2, 3, 4, 5 or 6, very preferably consisting exclusively of such recurring units.

Further preferred are mono-, oligo-, and polymers of formula I and I1 having identical recurring units.

Further preferred are mono-, oligo-, and polymers of formula I and I1 wherein $R^1$ and $R^2$ are identical groups.

Further preferred are mono-, oligo-, and polymers of formula I and I1 having a degree of polymerisation (number n of recurring units) from 2 to 5000, in particular from 10 to 5000, very preferably from 100 to 1000.

Further preferred are mono-, oligo-, and polymers of formula I and I1 having a molecular weight from 5000 to 30,000, in particular from 20,000 to 100,000.

Further preferred are mono-, oligo- and polymers of formula I and I1 comprising at least one reactive group P that is capable of a polymerisation or crosslinking reaction.

Further preferred are mono-, oligo-, and polymers of formula I and I1 that are mesogenic or liquid crystalline, in particular polymers forming calamitic phases, and reactive mesogens of formula I and I1 comprising one or more groups P—Sp—, forming calamitic phases.

Further preferred are mono-, oligo- and polymers of formula I and I1 wherein at least one of B and D is arylene or heteroarylene that is optionally substituted by one or more groups L.

L is F, Cl, Br, or an alkyl, alkoxy, alkylcarbonyl or alkoxycarbonyl group with 1 to 20 C atoms, wherein one or more H atoms are optionally replaced by F or Cl, further $C_1$–$C_{20}$-alkyl that is optionally substituted with one or more fluorine atoms, $C_1$–$C_{20}$-alkoxy, $C_1$–$C_{20}$-alkenyl, $C_1$–$C_{20}$-alkynyl, $C_1$–$C_{20}$-thioalkyl, $C_1$–$C_{20}$-silyl, $C_1$–$C_{20}$-ester, $C_1$–$C_{20}$-amino, $C_1$–$C_{20}$-fluoroalkyl, very preferably $C_1$–$C_{20}$-alkyl or $C_1$–$C_{20}$-fluoroalkyl.

Further preferred are mono-, oligo- and polymers of formula I and I1 shown above and below wherein
one of b and d is 0,
b and d are independently of each other 0, 1, 2, 3 or 4,
a and c are independently of each other 0, 1 or 2,
B and/or D are C≡C or arylene or heteroarylene,
B and/or D is $CX^1$=$CX^2$, wherein preferably at least one of $X^1$ and $X^2$ is different from H.
B and/or D is thiophene-2,5-diyl that is optionally mono- or polysubstituted by L as defined above,
B and/or D is thieno[3,2-b]thiophene that is optionally mono- or polysubstituted by L as defined above,
B and/or D is selected of formula III

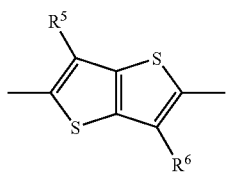

III wherein $R^5$ and $R^6$ have one of the meanings given for $R^1$ in formula I or of the preferred meanings below. Especially preferably $R^5$ and $R^6$ are alkyl or fluoroalkyl with 1 to 20 C-atoms.
n is an integer from 2 to 5000 and $R^1$ and $R^2$ are different from P—Sp— and P*—Sp, $R^1$ and $R^2$ are selected from H or $C_1$–$C_{20}$-alkyl that is optionally substituted with one or more fluorine atoms, $C_1$–$C_{20}$-alkoxy, $C_1$–$C_{20}$-alkenyl, $C_1$–$C_{20}$-alkynyl, $C_1$–$C_{20}$-thioalkyl, $C_1$–$C_{20}$-silyl, $C_1$–$C_{20}$-ester, $C_1$–$C_{20}$-amino, $C_1$–$C_{20}$-fluoroalkyl, and optionally substituted aryl or heteroaryl, very preferably $C_1$–$C_{20}$-alkyl or $C_1$–$C_{20}$-fluoroalkyl,
n is 1 and one or both of $R^3$ and $R^4$ are P—Sp— or P*—Sp—,
P* is —OH or —O—Si—$R^0R^{00}R^{000}$, preferably wherein $R^0$, $R^{00}$ and $R^{000}$ are identical or different groups selected from aryl or $C_{1-12}$-alkyl, preferably $C_1$–$C_6$-alkyl, like methyl, ethyl, isopropyl, tert-butyl or phenyl,
$R^3$ and $R^4$ are selected from H, halogen, $Sn(R^0)_3$, $CH_2Cl$, COH, CH=$CH_2$, $SiR^0R^{00}R^{000}$ and optionally substituted aryl or heteroaryl,
n≧1.

Copolymers according to the present invention wherein one or more of B and D are acetylene or arylene or heteroarylene have the following advantages:.
improved solubility through the use of side chains of the aryl co-polymers,
larger molecular weights, which leads to better processability.
improved packing by interdigitation of side-chains, which leads to liquid crystalline or crystalline polymers that facilitate charge transport.

If B or D is arylene or heteroarylene, it is preferably a mono-, bi- or tricyclic aromatic or heteroaromatic group with up to 25 C atoms, wherein the rings can be fused, and in which the heteroaromatic group contains at least one hetero ring atom, preferably selected from N, O and S. It is optionally substituted with one or more of F, Cl, Br, I, CN, and straight chain, branched or cyclic alkyl having 1 to 20 C atoms, which is unsubstituted, mono- or poly-substituted by F, Cl, Br, I, —CN or —OH, and in which one or more non-adjacent $CH_2$ groups are optionally replaced, in each case independently from one another, by —O—, —S—, —NH—, —$NR^0$—, —$SiR^0R^{00}$—, —CO—, —COO—, —OCO—, —OCO—O, —S—CO—, —CO—S—, —CH=CH— or —C≡C— in such a manner that O and/or S atoms are not linked directly to one another.

Preferred arylene or heteroarylene groups are selected from phenyl in which, in addition, one or more CH groups may be replaced by N, or naphthalene, alkyl fluorene or oxazole, thiophene, thienothiophene and dithienothiophene, wherein all these groups are optionally mono- or polysubstituted with L as defined above.

Especially preferred arylene or heteroarylene groups groups are 1,4-phenylene, fluorinated 1,4-phenylene, 2,5-pyridine, 2,5-pyrimidine, p,p'-biphenyl, naphthalene-2,6-diyl, thiophene-2,5-diyl, fluorinated or alkylated thiophene-2,5-diyl, 2,2-dithiophene, fluorinated or alkylated 2,2-dithiophene, [3,2-b]thiophene-2,5-diyl, fluorinated or alkylated thieno[3,2-b]thiophene-2,5-diyl, fluorinated benzo[1,2-b:4,5-b']dithiophene, 2,5-thiazole, 2,5-thiadiazole, 2,5-oxazole and 2,5-oxadiazole, all of which are unsubstituted, mono- or polysubstituted with L as defined above.

If one of $R^{1-4}$ is aryl or heteroaryl, it is preferably a mono-, bi- or tricyclic aromatic or heteroaromatic group with up to 25 C atoms, wherein the rings can be fused, and in which the heteroaromatic group contains at least one hetero ring atom, preferably selected from N, O and S. It is optionally substituted with one or more of F, Cl, Br, I, CN, and straight chain, branched or cyclic alkyl having 1 to 20 C atoms, which is unsubstituted, mono- or poly-substituted by F, Cl, Br, I, —CN or —OH, and in which one or more non-adjacent CH$_2$ groups are optionally replaced, in each case independently from one another, by —O—, —S—, —NH—, —NR$^0$—, —SiR$^0$R$^{00}$—, —CO—, —COO—, OCO—, —OCO—O, —S—CO—, —CO—S—, —CH=CH— or —C≡C— in such a manner that O and/or S atoms are not linked directly to one another.

Especially preferred aryl and heteroaryl groups are phenyl, fluorinated phenyl, pyridine, pyrimidine, biphenyl, naphthalene, optionally fluorinated or alkylated or fluoroalkylated benzo[1,2-b:4,5-b']dithiophene, optionally fluorinated or alkylated or fluoroalkylated thieno[3,2-b]thiophene, optionally fluorinated or alkylated or fluoroalkylated 2,2-dithiophene, thiazole and oxazole, all of which are unsubstituted, mono- or polysubstituted with L as defined above.

If one of R$^{1-4}$ is an alkyl or alkoxy radical, i.e. where the terminal CH$_2$ group is replaced by —O—, this may be straight-chain or branched. It is preferably straight-chain, has 2 to 8 carbon atoms and accordingly is preferably ethyl, propyl, butyl, pentyl, hexyl, heptyl, octyl, ethoxy, propoxy, butoxy, pentoxy, hexyloxy, heptoxy, or octoxy, furthermore methyl, nonyl, decyl, undecyl, dodecyl, tridecyl, tetradecyl, pentadecyl, nonoxy, decoxy, undecoxy, dodecoxy, tridecoxy or tetradecoxy, for example.

Fluoroalkyl or fluorinated alkyl or alkoxy is preferably straight chain (O)C$_i$F$_{2i+1}$, wherein i is an integer from 1 to 20, in particular from 1 to 15, very preferably (O)CF$_3$, (O)C$_2$F$_5$, (O)C$_3$F$_7$, (O)C$_4$F$_9$, (O)C$_5$F$_{11}$, (O)C$_6$F$_{13}$, (O)C$_7$F$_{15}$ or (O)C$_8$F$_{17}$, most preferably (O)C$_6$F$_{13}$.

CX$^1$=CX$^2$ is preferably —CH=CH—, —CH=CF—, —CF=CH—, —CF=CF—, —CH=C(CN)— or —C(CN)=CH—.

Halogen is preferably F, Br or Cl.

Hetero atoms are preferably selected from N, O and S.

The reactive or polymerisable group P is a group that is capable of participating in a polymerisation reaction, like radicalic or ionic chain polymerisation, polyaddition or polycondensation, or capable of being grafted, for example by condensation or addition, to a polymer backbone in a polymeranaloguous reaction. Especially preferred are polymerisable groups for chain polymerisation reactions, like radicalic, cationic or anionic polymerisation. Very preferred are polymerisable groups comprising a C—C double or triple bond, and polymerisable groups capable of polymerisation by a ring-opening reaction, like oxetanes or epoxides.

The polymerisable or reactive group P is preferably selected from

CH$_2$=CW$^1$—COO—,

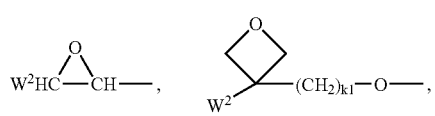

CH$_2$=CW$^2$—(O)$_{k1}$—, CH$_3$—CH=CH—O—, (CH$_2$=CH)$_2$ CH—OCO—, (CH$_2$=CH)$_2$CH—O—, (CH$_2$=CH—CH$_2$)$_2$ CH—OCO—, (CH$_2$=CH—CH$_2$)$_2$N—, HO—CW$^2$W$^3$—, HS—CW$^2$W$^3$—, HW$^2$N—, HO—CW$^2$W$^3$—NH—, CH$_2$=CW$^1$—CO—NH—, CH$_2$=CH—(COO)$_{k1}$—Phe-(O)$_{k2}$—, Phe-CH=CH—, HOOC—, OCN—, and W$^4$W$^5$W$^6$Si—, with W$^1$ being H, Cl, CN, phenyl or alkyl with 1 to 5 C-atoms, in particular H, Cl or CH$_3$, W$^2$ and W$^3$ being independently of each other H or alkyl with 1 to 5 C-atoms, in particular methyl, ethyl or n-propyl, W$^4$, W$^5$ and W$^6$ being independently of each other Cl, oxaalkyl or oxacarbonylalkyl with 1 to 5 C-atoms, Phe being 1,4-phenylene and k$_1$ and k$_2$ being independently of each other 0 or 1.

Especially preferred groups P are CH$_2$=CH—COO—, CH$_2$=C(CH$_3$)—COO—, CH$_2$=CH—, CH$_2$=CH—O—, (CH$_2$=CH)$_2$CH—OCO—, (CH$_2$=CH)$_2$CH—O—, and

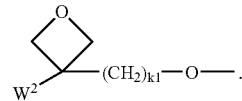

Very preferred are acrylate and oxetane groups. Oxetanes produce less shrinkage upon polymerisation (cross-linking), which results in less stress development within films, leading to higher retention of ordering and fewer defects. Oxetane cross-linking also requires cationic initiator, which unlike free radical initiator is inert to oxygen.

As for the spacer group Sp all groups can be used that are known for this purpose to the skilled in the art. The spacer group Sp is preferably of formula Sp'—X, such that P—Sp—is P—Sp'—X—and P*—Sp— is P*—Sp'—X—, wherein Sp' is alkylene with up to 20 C atoms which may be unsubstituted, mono- or poly-substituted by F, Cl, Br, I or CN, it being also possible for one or more non-adjacent CH$_2$ groups to be replaced, in each case independently from one another, by —O—, —S—, —NH—, —NR$^0$—, —SiR$^0$R$^{00}$, —CO—, —COO—, —OCO—, —OCO—O—, —S—CO—, —CO—S—, —CH=CH— or —C≡C— in such a manner that O and/or S atoms are not linked directly to one another, X is —O—, —S—, —CO—, —COO—, —OCO—, —O—COO—, —CO—NR$^0$—, —NR$^0$—CO—, —OCH$_2$—, —CH$_2$O—, —SCH$_2$—, —CH$_2$S—, —CF$_2$O—, —OCF$_2$—, —CF$_2$S—, —SCF$_2$—, —CF$_2$CH$_2$—, —CH$_2$CF$_2$—, —CF$_2$CF$_2$—, —CH=N—, —N=CH—, —N=N—, —CH=CR$^0$—, —CX$^1$=CX$^2$—, —C≡C—, —CH=CH—COO—, —OCO—CH=CH— or a single bond, and R$^0$, R$^{00}$, X$^1$ and X$^2$ have one of the meanings given above.

X is preferably —O—, —S—, —OCH$_2$—, —CH$_2$O—, —SCH$_2$—, —CH$_2$S—, —CF$_2$O—, —OCF$_2$—, —CF$_2$S—, —SCF$_2$—, —CH$_2$CH$_2$—, —CF$_2$CH$_2$—, —CH$_2$CF$_2$—, —CF$_2$CF$_2$—, —CH=N—, —N=CH—, —N=N—, —CH=CR$^0$—, —CX$^1$=CX$^2$—, —C≡C— or a single bond, in particular —O—, —C—C—, —CX$^1$=CX$^2$— or a single bond, very preferably a group that is able to from a conjugated system, such as —C—C— or —CX$^1$=CX$^2$—, or a single bond.

Typical groups Sp' are, for example, —(CH$_2$)$_p$—, —(CH$_2$CH$_2$O)$_q$—CH$_2$CH$_2$—, —CH$_2$CH$_2$—S—CH$_2$CH$_2$— or —CH$_2$CH$_2$—NH—CH$_2$CH$_2$— or —(SiR$^0$R$^{00}$—O)$_p$—, with p being an integer from 2 to 12, q being an integer from 1 to 3 and R$^0$ and R$^{00}$ having the meanings given above.

Preferred groups Sp' are ethylene, propylene, butylene, pentylene, hexylene, heptylene, octylene, nonylene, decylene, undecylene, dodecylene, octadecylene, ethyleneoxyethylene, methyleneoxybutylene, ethylene-thioethylene, ethylene-N-methyl-iminoethylene, 1-methylalkylene, ethenylene, propenylene and butenylene for example.

Further preferred are compounds with one or two groups P—Sp—or P*—Sp— wherein Sp is a single bond.

In case of compounds with two groups P—Sp or P*—Sp—, respectively, each of the groups P or P* and the spacer groups Sp can be identical or different.

Another preferred embodiment relates to compounds comprising one or more groups P*—Sp—, wherein P* is a group that can be converted to or substituted by a polymerisable or reactive group P as defined above. Preferably P* is a group that is less reactive than P, for example towards spontaneous polymerisation. These compounds can be used for example as intermediates in the synthesis of polymerisable compounds of formula I1 having one or more groups P, or as a precursor material for polymerisable compounds which are too reactive to be stored or transported for longer periods of time. The group P* is preferably chosen such that it can easily be transformed into or substituted by a group P by known methods. For example, it can be a protected form of group P. Further preferred groups P* are for example —OH or silyl groups like —O—Si—$R^oR^{oo}R^{ooo}$, for example —O—Si(CH$_3$)$_3$, —O—Si-(isopropyl)$_3$, —O—Si-(phenyl)$_3$, —O—Si—(CH$_3$)$_2$(phenyl), —O—Si(CH$_3$)$_2$(tert-butyl) or the like, which can be reacted e.g. into polymerisable (meth)acrylate end groups.

SCLCPs obtained from the inventive compounds or mixtures by polymerisation or copolymerisation have a backbone that is formed by the polymerisable group P.

Especially preferred are mono-, oligo- and polymers selected from the following formulae

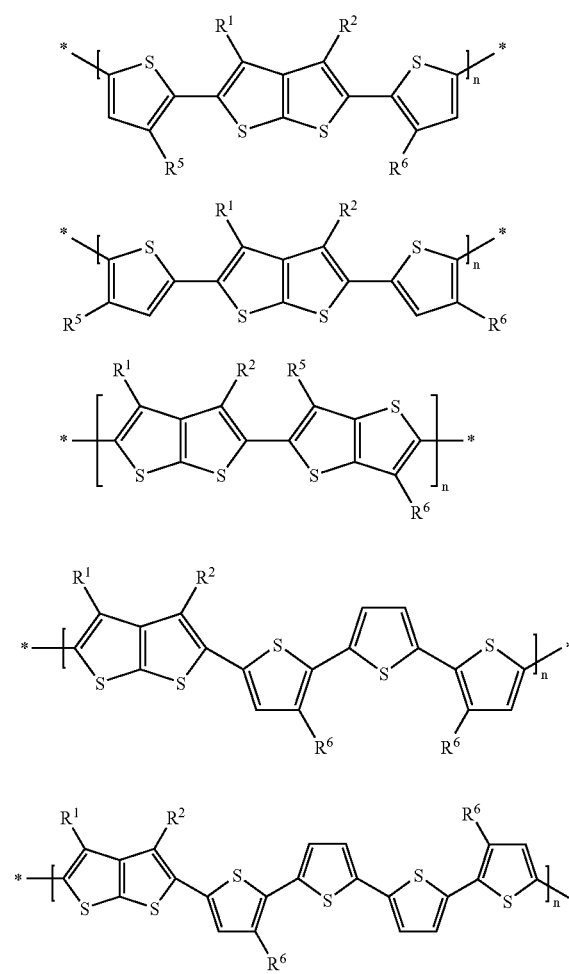

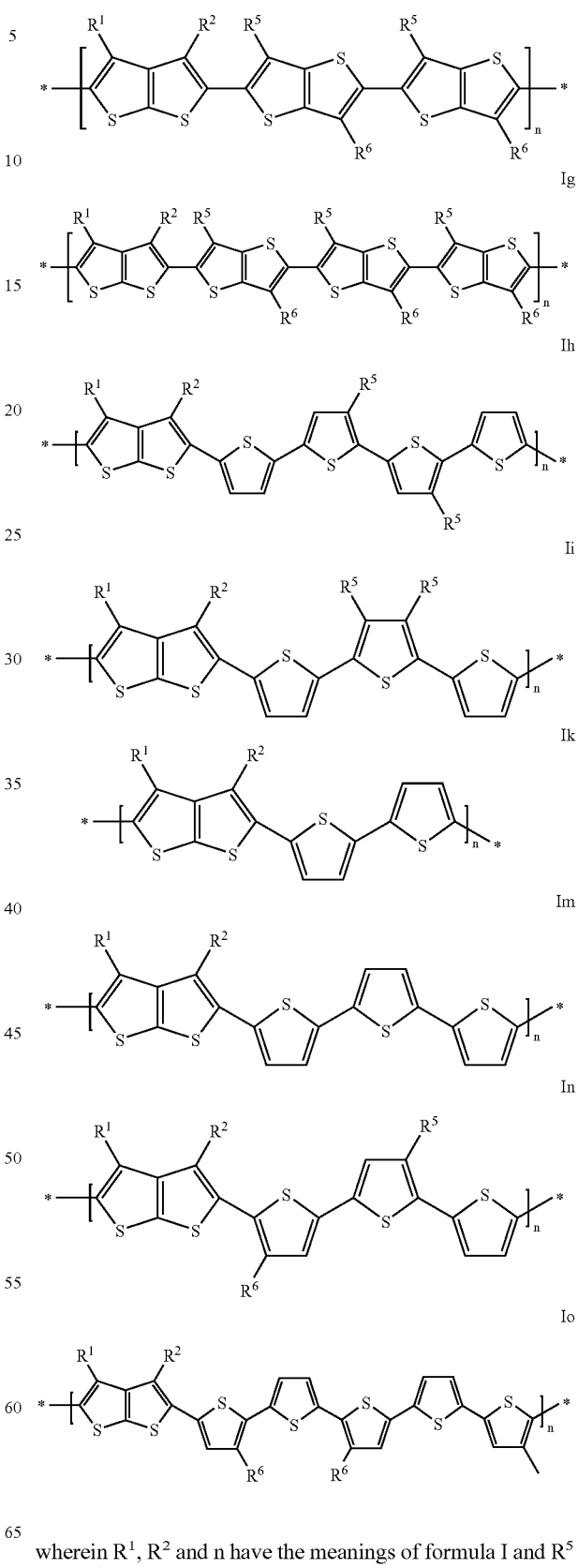

wherein $R^1$, $R^2$ and n have the meanings of formula I and $R^5$ and $R^6$ have one of the meanings of formula III or the preferred meanings above. Especially preferably $R^1$, $R^2$, $R^5$ and $R^6$ in these formulae are alkyl or fluoroalkyl with 1 to 20 C-atoms.

Further preferred are the following monomeric compounds

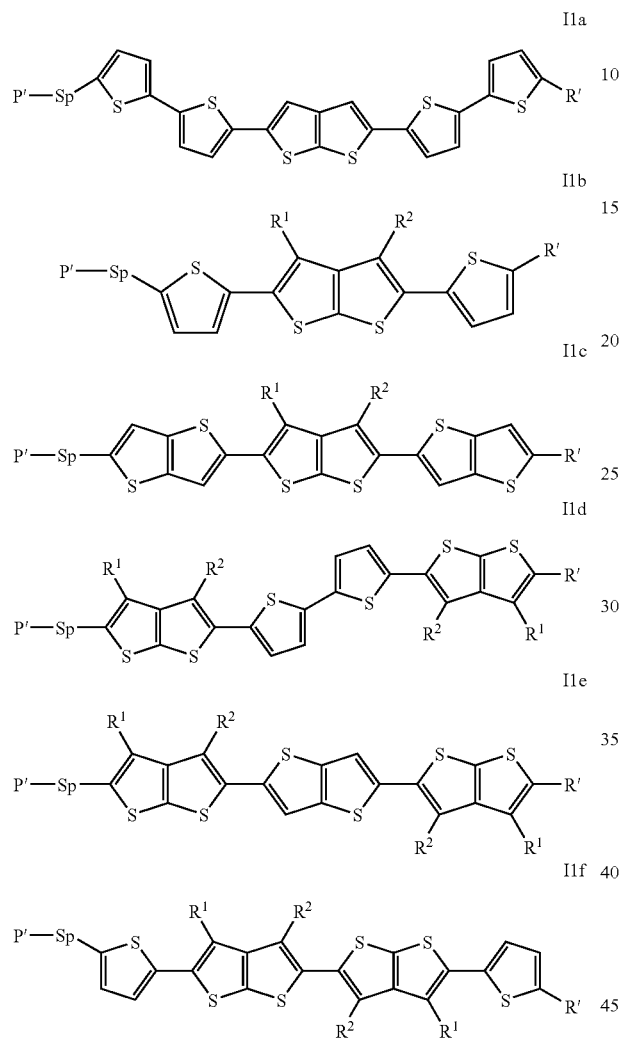

wherein $R^1$, $R^2$ and Sp are as defined in formula I, P' is P or P* as defined in formula I, and R' has one of the meanings of $R^3$ given in formula I1.

The mono-, oligo- and polymers of the present invention can be synthesized according to or in analogy to known methods. Some preferred methods are described below.

The di-esters of thieno[2,3-b]thiophene are synthesised according to literature methods as shown in Scheme 1 [see A. Comel; G. Kirsch, *J. Heterocyclic Chem*, 2001, 38, 1167–1171]. Therefore an active methylene compound such as malonitrile or penta-2,4-dione is reacted with carbon disulfide and ethyl bromoacetate in the presence of base affords the thieno-2,3-b-thiophene ring. Longer aliphatic chains can readily by introduced onto the core by varying the active methylene compound used. For the unsubstituted compound, the amino groups are removed by diazotisation and subsequent treatment with hypophosphorous acid. Finally the ester groups are hydrolysed to the corresponding carboxylic acids, and these are converted directly to the aromatic bromides by treatment with NBS in the presence of sodium hydroxide. An alternative route to the unsubstituted thieno[2,3-b]thiophene core is depected in Scheme 2. Commercially available thiophene-2-thiol is alklylated with bromoacetaldehyde dimethyl acetal and the resulting protected aldehyde in deprotected and cyclised to the product in one-pot by treatment with polyphosphoric acid in refluxing chlorobenzene. Unsubstituted thieno[2,3-b]thiophene can readily be converted to the 2,5-dibromo or 2,5-diiodothieno [2,3-b]thiophene by lithiation with two equivalents of a halogenating agent. 2-Bromo-5-iodo-thieno[2,3-b] thiophene can be prepared by a sequential two step electrophillic bromination and iodination as depected in Scheme 3.

Scheme 1:
Synthesis of dibromo-thieno[2,3-b]thiophene derivatives.

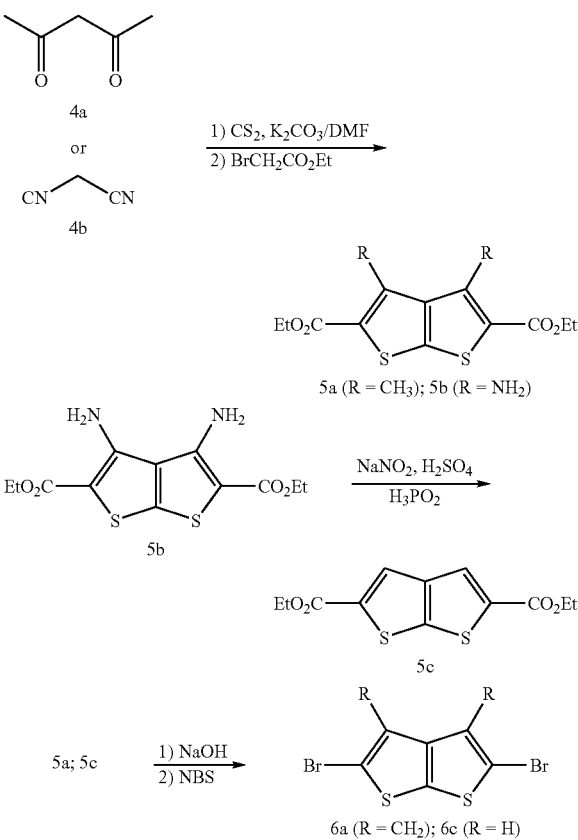

Scheme 2:
Alternative synthesis of thieno[2,3-b]thiophene.

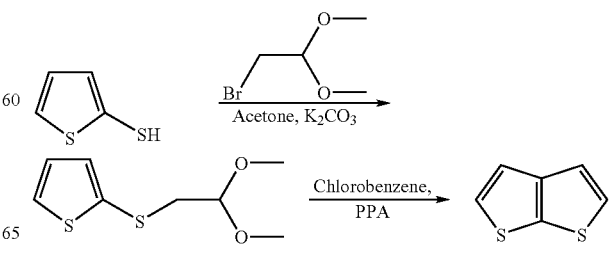

Scheme 3:
Synthesis of halogenated-thieno[2,3-b]thiophenes.

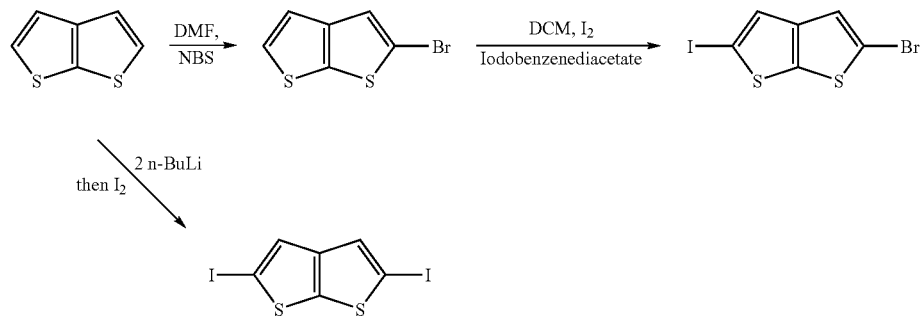

The dihalo intermediates are then reacted with thiophene boronic acids under cross-coupling conditions, or with thiophene organozinc reagents in the presence of palladium catalyst to afford the bis(thiophene) intermediates, as shown in Scheme 4. These are subsequently polyrerised oxidatively by treatment with ferric chloride to afford polymers of reasonable molecular weight (Mw=14,000–23,000).

reagent of thieno[2,3-b]thiophene is reacted with a dihalo aromatic compound (Scheme 5). By modifying the ratio of the starting reagents, the percentage incorporation of the thieno-2,3-thiophene, and hence the HOMO level, can easily be modified, as seen in Scheme 6.

Scheme 4:
Synthesis of thiophene co-polymers.

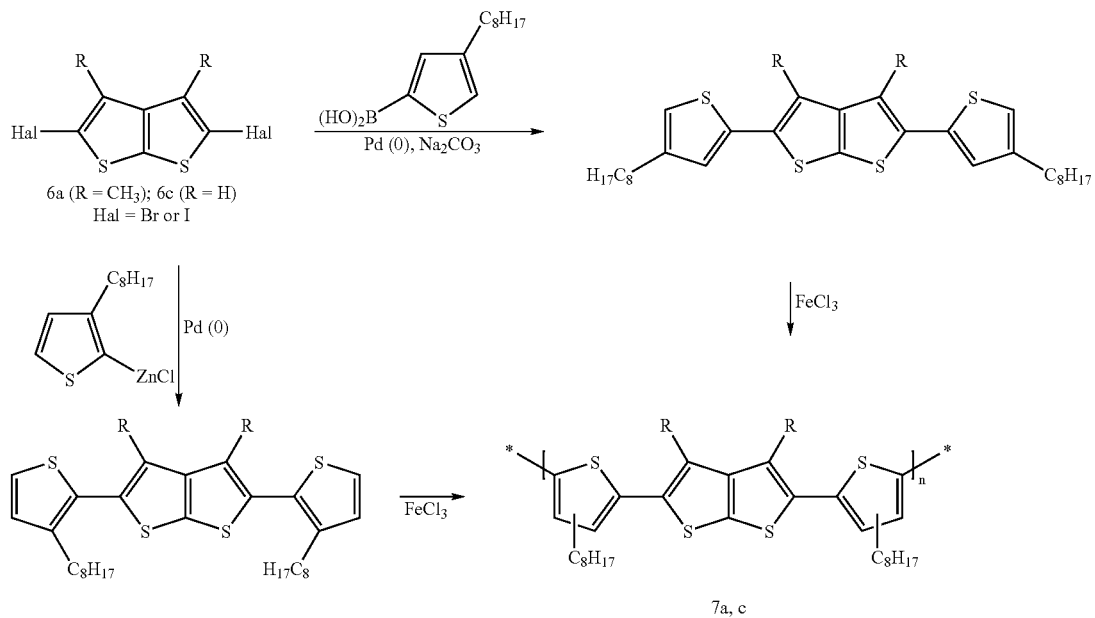

Other co-polymers are readily formed by reaction of a 2,5-dihalothieno[2,3-b]thiophene with, for example, a bis(boronic) ester or acid under Suzuki conditions (see M. Jayakannan, J. L. J. van Dongen, R. A. J. Janssen, Macromolecules, 2001, 34, p5386–5393)) or a bis(organo)tin reagent under Stille conditions (see B. Tsuie et al, *J. Mater. Chem.*, 1999, 9, p2189–2200), as shown in Scheme 5. The methodology can be reversed so that the bis(boronic) ester or acid of thieno[2,3-b]thiophene, or the bis(organo)tin Scheme 5:
Synthesis of 1:1 co-polymers.

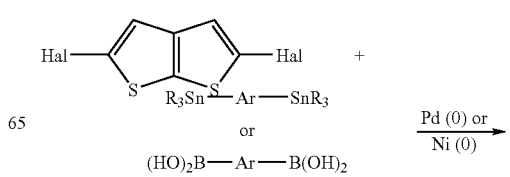

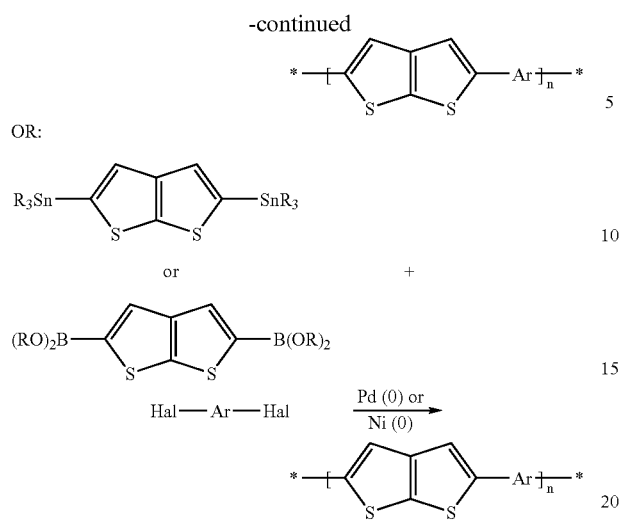

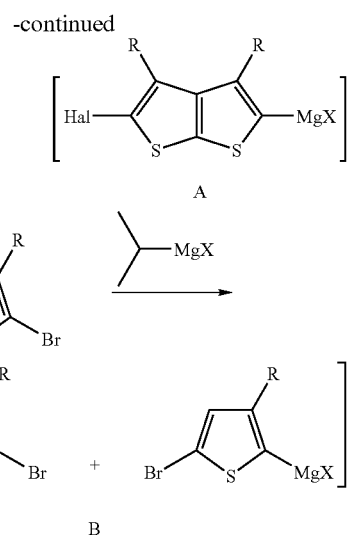

Scheme 6:
Example of the synthesis of a random co-polymer.

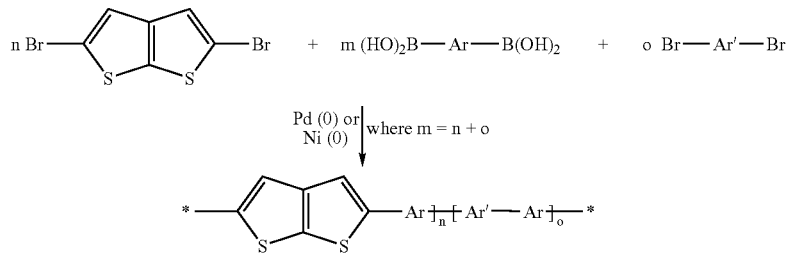

wherein Ar has one of the meanings of B given in formula I.

Thieno-2,3-b-thiophene is also readily incorporated into regioregular poly(alkyl)thiophene, and this provides a means to improve the air-stability of that polymer without adversely affecting the close-packed morphology which contributes to such high charge carrier mobilities for PAT. The method of synthesis is outlined in scheme 7, as is based upon the route described by McCullough et al. [see S. M. K. Robert S. Loewe, and; R. D. McCullough*, Adv. Mater., 1999, 11, 250]. Therefore the mono-Grignard reagent of 2,5-dibromo-3-alkylthiophene and thieno-2,3-b-thiophene are formed in separate flask by treatment with 1 equivalent of an alkyl Grignard reagent or by treatment with magnesium metal. These 2 reagents are then pre-mixed and treated with a catalytic amount of nickel to initiate polymerisation. Both reagents have similar reactivity and the thieno-2,3-b-thiophene is incorporated randomly along the backbone. A typical ratio would be 5–20%.

Scheme 7:
Incorporation into a regioregular poly(alkyl)thiophene.

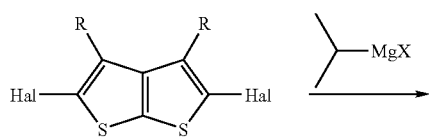

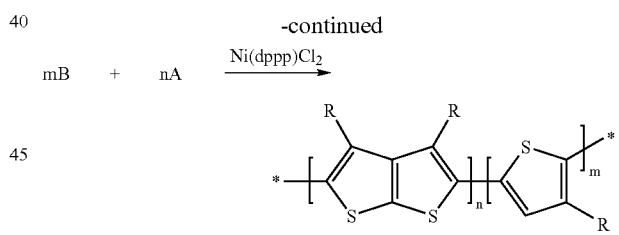

A further aspect of the invention relates to both the oxidised and reduced form of the compounds and materials according to this invention. Either loss or gain of electrons results in formation of a highly delocalised ionic form, which is of high conductivity. This can occur on exposure-to common dopants. Suitable dopants and methods of doping are known to those skilled in the art, e.g. from EP 0 528 662, U.S. Pat. No. 5,198,153 or WO 96/21659.

The doping process typically implies treatment of the semiconductor material with an oxidating or reducing agent in a redox reaction to form delocalised ionic centres in the material, with the corresponding counterions derived from the applied dopants; Suitable doping methods comprise for example exposure to a doping vapor in the atmospheric pressure or at a reduced pressure, electrochemical doping in a solution containing a dopant, bringing a dopant into contact with the semiconductor material to be thermally diffused, and ion-implantantion of the dopant into the semiconductor material.

When electrons are used as carriers, suitable dopants are for example halogens (e.g., $I_2$, $Cl_2$, $Br_2$, ICl, $ICl_3$, IBr and IF), Lewis acids (e.g., $PF_5$, $AsF_5$, $SbF_5$, $BF_3$, $BCl_3$, $SbCl_5$, $BBr_3$ and $SO_3$), protonic acids, organic acids, or amino acids (e.g., HF, HCl, $HNO_3$, $H_2SO_4$, $HClO_4$, $FSO_3H$ and $ClSO_3H$), transition metal compounds (e.g., $FeCl_3$, FeOCl, $Fe(ClO_4)_3$, $Fe(4-CH_3C_6H_4SO_3)_3$, $TiCl_4$, $ZrCl_4$, $HfCl_4$, $NbF_5$, $NbCl_5$, $TaCl_5$, $MoF_5$, $MoCl_5$, $WF_5$, $WCl_6$, $UF_6$ and $LnCl_3$ (wherein Ln is a lanthanoid), anions (e.g., $Cl^-$, $Br^-$, $I^-$, $I_3^-$, $HSO_4^-$, $SO_4^{2-}$, $NO_3^-$, $ClO_4^-$, $BF_4^-$, $PF_6^-$, $AsF_6^-$, $SbF_6^-$, $FeCl_4^-$, $Fe(CN)_6^{3-}$, and anions of various sulfonic acids, such as aryl-$SO_3^-$). When holes are used as carriers, examples of dopants are cations (e.g., $H^+$, $Li^+$, $Na^+$, $K^+$, $Rb^+$ and $Cs^+$), alkali metals (e.g., Li, Na, K, Rb, and Cs), alkaline-earth metals (e.g., Ca, Sr, and Ba), $O_2$, $XeOF_4$, $(NO_2^+)$ $(SbF_6^-)$, $(NO_2^+)$ $(SbCl_6^-)$, $(NO_2^+)$ $(BF_4^-)$, $AgClO_4$, $H_2IrCl_6$, $La(NO_3)_3 \cdot 6H_2O$, $FSO_2OOSO_2F$, Eu, acetylcholine, $R_4N^+$, (R is an alkyl group), $R_4P^+$ (R is an alkyl group), $R_6As^+$ (R is an alkyl group), and $R_3S^+$ (R is an alkyl group).

The conducting form of the compounds and materials of the present invention can be used as an organic "metal" in applications, for example, but not limited to, charge injection layers and ITO planarising layers in organic light emitting diode applications, films for flat panel displays and touch screens, antistatic films, printed conductive substrates, patterns or tracts in electronic applications such as printed circuit boards and condensers.

A preferred embodiment of the present invention relates to mono-, oligo- and polymers of formula I and its preferred subformulae that are mesogenic or liquid crystalline, and very preferably comprise one or more polymerisable groups. Very preferred materials of this type are monomers and oligomers of formula I and its preferred subformulae wherein n is an integer from 1 to 15 and $R^3$ and/or $R^4$ denote P—Sp—.

These materials are particularly useful as semiconductors or charge transport materials, as they can be aligned into uniform highly ordered orientation in their liquid crystal phase by known techniques, thus exhibiting a higher degree of order that leads to particularly high charge carrier mobility. The highly ordered liquid crystal state can be fixed by in situ polymerisation or crosslinking via the groups P to yield polymer films with high charge carrier mobility and high thermal, mechanical and chemical stability.

For example, if a device is made from a polymerisable liquid crystal material by polymerisation in situ, the liquid crystal material preferably comprises one or more mono- or oligomers of formula I and its preferred subformulae wherein one or both of $R^3$ and $R^4$ denote P—Sp—. If a liquid crystal polymer is prepared first, for example by polymerisation in solution, and the isolated polymer is used to make the device, the polymer is preferably made from a liquid crystal material comprising one or more mono- or oligomers of formula I and its preferred subformulae wherein one of $R^3$ and $R^4$ denotes P—Sp—.

It is also possible to copolymerise the polymerisable mono-, oligo- and polymers according to the present invention with other polymerisable mesogenic-or liquid crystal monomers that are known from prior art, in order to induce or enhance liquid crystal phase behaviour.

Thus, another aspect of the invention relates to a polymerisable liquid crystal material comprising one or more mono-, oligo- or polymers of the present invention as described above and below comprising at least one polymerisable group, and optionally comprising one or more further polymerisable compounds, wherein at least one of the polymerisable mono-, oligo- and polymers of the present invention and/or the further polymerisable compounds is mesogenic or liquid crystalline.

Particularly preferred are liquid crystal materials having a nematic and/or smectic phase. For FET applications smectic materials are especially preferred. For OLED applications nematic or smectic materials are especially preferred.

Another aspect of the present invention relates to an anisotropic polymer film with charge transport properties obtainable from a polymerisable liquid crystal material as defined above that is aligned in its liquid crystal phase into macroscopically uniform orientation and polymerised or crosslinked to fix the oriented state.

Preferably polymerisation is carried out as in-situ polymerisation of a coated layer of the material, preferably during fabrication of the electronic or optical device comprising the inventive semiconductor material. In case of liquid crystal materials, these are preferably aligned in their liquid crystal state into homeotropic orientation prior to polymerisation, where the conjugated pi-electron systems are orthogonal to the direction of charge transport. This ensures that the intermolecular distances are minimised and hence then energy required to transport charge between molecules is minimised. The molecules are then polymerised or crosslinked to fix the uniform orientation of the liquid crystal state. Alignment and curing are carried out in the liquid crystal phase or mesophase of the material. This technique is known in the art and is generally described for example in D. J. Broer, et al., Angew. Makromol. Chem. 183, (1990), 45–66

Alignment of the liquid crystal material can be achieved for example by treatment of the substrate onto which the material is coated, by shearing the material during or after coating, by application of a magnetic or electric field to the coated material, or by the addition of surface-active compounds to the liquid crystal material. Reviews of alignment techniques are given for example by I. Sage in "Thermotropic Liquid Crystals", edited by G. W. Gray, John Wiley & Sons, 1987, pages 75–77, and by T. Uchida and H. Seki in "Liquid Crystals—Applications and Uses Vol. 3", edited by B. Bahadur, World Scientific Publishing, Singapore 1992, pages 1–63. A review of alignment materials and techniques is given by J. Cognard, Mol. Cryst. Liq. Cryst. 78, Supplement. (1981), pages 1–77.

Polymerisation takes place by exposure to heat or actinic radiation. Actinic radiation means irradiation with light, like UV light, IR light or visible light, irradiation with X-rays or gamma rays or irradiation with high energy particles, such as ions or electrons. Preferably polymerisation is carried out by UV irradiation at a non-absorbing wavelength. As a source for actinic radiation for example a single UV lamp or a set of UV.lamps can be used. When using a high lamp power the curing time can be reduced. Another possible source for actinic radiation is a laser, like e.g. a UV laser, an IR laser or a visible laser.

Polymerisation is preferably carried out in the presence of an initiator absorbing at the wavelength of the actinic radiation. For example, when polymerising by means of UV light, a photoinitiator can be used that decomposes under UV irradiation to produce free radicals or ions that start the polymerisation reaction. When curing polymerisable materials with acrylate or methacrylate groups, preferably a radical photoinitiator is used, when curing polymerisable materials with vinyl, epoxide and oxetane groups, preferably a cationic photoinitiator is used. It is also possible to use a polymerisation initiator that decomposes when heated to produce free radicals or ions that start the polymerisation. As a photoinitiator for radical polymerisation for example the commercially available Irgacure 651, Irgacure 184, Darocure 1173 or Darocure 4205 (all from Ciba Geigy AG) can be used, whereas in case of cationic photopolymerisation the commercially available UVI 6974 (Union Carbide) can be used.

The polymerisable material can additionally comprise one or more other suitable components such as, for example, catalysts, sensitizers, stabilizers, inhibitors, chain-transfer agents, co-reacting monomers, surface-active compounds, lubricating agents, wetting agents, dispersing agents, hydrophobing agents, adhesive agents, flow improvers, defoaming agents, deaerators, diluents, reactive diluents, auxiliaries, colourants, dyes or pigments.

Mono-, oligo- and polymers comprising one or more groups P—Sp—can also be copolymerised with polymerisable mesogenic compounds to induce or enhance liquid crystal phase behaviour. Polymerisable mesogenic compounds that are suitable as comonomers are known in prior art and disclosed for example in WO 93/22397; EP 0,261, 712; DE 195,04,224; WO 95/22586 and WO 97/00600.

Another aspect of the invention relates to a liquid crystal side chain polymer (SCLCP) obtained from a polymerisable liquid crystal material as defined above by polymerisation or polymeranaloguous reaction. Particularly preferred are SCLCPs obtained from one or more monomers of formula I1 and its preferred subformulae wherein one or both, preferably one, of $R^3$ and $R^4$ are a polymerisable or reactive group, or from a polymerisable mixture comprising one or more of said monomers.

Another aspect of the invention relates to an SCLCP obtained from one or more monomers of formula I1 and its preferred subformulae wherein one or both of $R^3$ and $R^4$ are a polymerisable group, or from a polymerisable liquid crystal mixture as defined above, by copolymerisation or polymeranaloguous reaction together with one or more additional mesogenic or non-mesogenic comonomers.

Side chain liquid crystal polymers or copolymers (SCLCPs), in which the semiconducting component is located as a pendant group, separated from a flexible backbone by an aliphatic spacer group, offer the possibility to obtain a highly ordered lamellar like morphology. This structure consists of closely packed conjugated aromatic mesogens, in which very close (typically <4 Å) pi-pi stacking can occur. This stacking allows intermolecular charge transport to occur more easily, leading to high charge carrier mobilities. SCLCPs are advantageous for specific applications as they can be readily synthesized before processing and then e.g. be processed from solution in an organic solvent. If SCLCPs are used in solutions, they can orient spontaneously when coated onto an appropriate surface and when at their mesophase temperature, which can result in large area, highly ordered domains.

SCLCPs can be prepared from the polymerisable compounds or mixtures according to the invention by the methods described above, or by conventional polymerisation techniques which are known to those skilled in the art, including for example radicalic, anionic or cationic chain polymerisation, polyaddition or polycondensation. Polymerisation can be carried out for example as polymerisation in solution, without the need of coating and prior alignment, or polymerisation in situ. It is also possible to form SCLCPs by grafting compounds according to the invention with a suitable reactive group, or mixtures thereof, to presynthesized isotropic or anisotropic polymer backbones in a polymeranaloguous reaction. For example, compounds with a terminal hydroxy group can be attached to polymer backbones with lateral carboxylic acid or ester groups, compounds with terminal isocyanate groups can be added to backbones with free hydroxy groups, compounds with terminal vinyl or vinyloxy groups can be added, e.g., to polysiloxane backbones with Si—H groups. It is also possible to form SCLCPs by copolymerisation or polymeranaloguous reaction from the inventive compounds together with conventional mesogenic or non mesogenic comonomers. Suitable comonomers are known to those skilled in the art. In principle it is possible to use all conventional comonomers known in the art that carry a reactive or polymerisable group capable of undergoing the desired polymer-forming reaction, like for example a polymerisable or reactive group P as defined above. Typical mesogenic comonomers are for example those mentioned in WO 93/22397, EP 0 261 712, DE 195 04 224, WO 95/22586, WO 97/00600 and GB 2 351 734. Typical non mesogenic comonomers are for example alkyl acrylates or alkyl methacrylates with alkyl groups of 1 to 20 C atoms, like methyl acrylate or methyl methacrylate.

The mono-, oligo- and polymers of the present invention are useful as optical, electronic and semiconductor materials, in particular as charge transport materials in field effect transistors (FETs), e.g., as components of integrated circuitry, ID tags or TFT applications. Alternatively, they may be used in organic light emitting diodes (OLEDs) in electroluminescent display applications or as backlight of, e.g., liquid crystal displays, as photovoltaics or sensor materials, for electrophotographic recording, and for other semiconductor applications.

Especially the oligomers and polymers according to the invention show advantageous solubility properties which allow production processes using solutions of these compounds. Thus films, including layers and coatings, may be generated by low cost production techniques, e.g., spin coating. Suitable solvents or solvent mixtures comprise alkanes and/or aromatics, especially their fluorinated derivatives.

The materials of the present invention are useful as optical, electronic and semiconductor materials, in particular as charge transport materials in field effect transistors (FETs), as photovoltaics or sensor materials, for electrophotographic recording, and for other semiconductor applications. Such FETs, where an organic semiconductive material is arranged as a film between a gate-dielectric and a drain and a source electrode, are generally known, e.g., from U.S. Pat. No. 5,892,244, WO 00/79617, U.S. Pat. No. 5,998,804, and from the references cited in the background and prior art chapter and listed below. Due to the advantages, like low cost production using the solubility properties of the compounds according to the invention and thus the processibility of large surfaces, preferred applications of these FETs are such as integrated circuitry, TFT-displays and security applications.

In security applications, field effect transistors and other devices with semiconductive materials, like transistors or diodes, may-be used for ID tags or security markings to authenticate and prevent counterfeiting of documents of value like banknotes, credit cards or ID cards, national ID documents, licenses or any product with monetry value, like stamps, tickets, shares, cheques etc.

Alternatively, the mono-, oligo- and polymers according to the invention may be used in organic light emitting devices or diodes (OLEDs), e.g., in display applications or as backlight of e.g. liquid crystal displays. Common OLEDs are realized using multilayer structures. An emission layer is generally sandwiched between one or more electron-transport and/or hole-transport layers. By applying an electric voltage electrons and holes as charge carriers move towards the emission layer where their recombination leads to the excitation and hence luminescence of the lumophor units contained in the emission layer. The inventive compounds, materials and films may be employed in one or more of the charge transport layers and/or in the emission layer, corresponding to their electrical and/or optical properties. Furthermore their use within the emission layer is especially advantageous, if the compounds, materials and films according to the invention show electroluminescent properties themselves or comprise electroluminescent groups or compounds. The selection, characterization as well as the processing of suitable monomeric, oligomeric and polymeric compounds or materials for the use in OLEDs is generally known by a person skilled in the art, see, e.g., Meerholz, Synthetic Materials, 111–112, 2000,31–34, Alcala, J. Appl. Phys., 88, 2000, 7124–7128 and the literature cited therein.

According to another use, the inventive compounds, materials or films, especially those which show photoluminescent properties, may be employed as materials of light sources, e.g., of display devices such as described in EP 0 889 350 A1 or by C. Weder et al., Science, 279, 1998, 835–837.

According to another use, the inventive compounds, materials or films can be used alone or together with other materials in or as alignment layers in LCD or OLED devices, as described for example in U.S. 2003/0021913. The use of charge transport compounds according to the present invention can increase the electrical conductivity of the alignment layer. When used in an LCD, this increased electrical conductivity can reduce adverse residual dc effects in the switchable LCD cell and suppress image sticking or, for example in ferroelectric LCDs, reduce the residual charge produced by the switching of the spontaneous polarisation charge of the ferroelectric LCs. When used in an OLED device comprising a light emitting material provided onto the alignment layer, this increased electrical conductivity can enhance the electroluminescence of the light emitting material. The compounds or materials according to the present invention having mesogenic or liquid crystalline properties can form oriented anisotropic films as described above, which are especially useful as alignment layers to induce or enhance alignment in a liquid crystal medium provided onto said anisotropic film. The materials according to the present invention may also be combined with photoisomerisable compounds and/or chromophores for use in or as photoalignment layers, as described in U.S. 2003/0021913.

The examples below serve to illustrate the invention without limiting it. In the foregoing and the following, all temperatures are given in degrees Celsius, and all percentages are by weight, unless stated otherwise.

EXAMPLE 1

Polymer 8 has been synthesised according to Scheme 4 above.

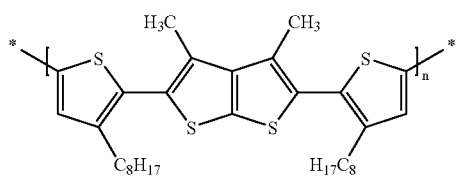

8

2,5-Dibromo-3,4-dimethylthieno[2,3-b]thiophene

To a solution of 3,4-dimethylthieno[2,3-b]thiophene-2,5-dicarboxylic acid (28.0g, 0.11 mol) in NMP (800 ml) and water (50 ml) was added NBS (44 g, 0.25 mol) portionwise over 30 min. The mixture for stirred for 16 h at RT and poured into water (1 L). The resultant precipitate was filtered and dried under vacuum. Purification by flash chromatography over silica (eluent: petrol) afforded the product as white crystals (27.4 g, 77%). M/Z (326, t, M$^+$). NMR gave the expected signals.

2,5-Bis(3-octylthiophen-2-yl)-3,4-dimethylthieno[2,3-b]thiophene

To a solution of 2-bromo-3-octylthiophene (4.0 g, 14.5 mmol) in dry THF (20 ml) under nitrogen was added a solution of Rieke zinc (Aldrich, 1.1 g 20 ml of THF, 17 mmol) at −78° C. The solution was allowed to warm to RT and stirred for 16 h. Stirring was stopped and the solution allowed to settle for 2 h. The resultant solution was transferred by cannula into a flask containing 2,5-dibromo-3,4-dimethylthieno[2,3-b]thiophene (1.28 g, 3.9 mmol), degassed THF (50 ml) and [1,1′-bis(diphenylphosphino)ferrocene]palladium(II) chloride (64 mg, 2 mol %) at 0° C. The reaction was warmed to RT over 30 min, and then refluxed for 24 h. The reaction was cooled and quenched with 5% HCL. The resultant mixture was extracted with ethyl acetate (3×50 ml), and the combined organics were washed with brine, dried (Na$_2$SO$_4$), filtered and concentrated under reduced pressure. The crude product was purified by flash chromatography over silica (eluent: petrol), followed by reverse phase chromatography (eluent: CH$_3$CN/THF 2:1) to afford the product as a colourless oil (1.56 g, 72%). M/Z 556 (M$^+$). Found C, 69.1%, H, 7.6%. Calc. for C$_{32}$H$_{44}$S$_4$ C, 69.0; H 8.0. NMR gave the expected signals.

Poly(2,5-Bis(3-octylthiophen-2-yl)-3,4-dimethylthieno[2,3-b]thiophene) (8)

To a solution of 2,5-bis(3-octylthiophen-2-yl)-3,4-dimethylthieno[2,3-b]thiophene (0.71 g, 1.28 mmol) in dry chloroform (20 ml) was added a solution of anhydrous ferric chloride (1.0 g, 6. 2 mmol) in chloroform (110 ml) dropwise. A constant stream of nitrogen was passed through the solution to remove HCl formed during the reaction. The reaction was stirred for 18 h at 25° C, and then poured into methanol (500 ml). After stirring for 30 min the solution was filtered and washed with water and methanol. The resulting yellow solid was stirred in conc. ammonia solution for 1 h, filtered and dried. The solid was extracted with methanol (soxhlet), iso-hexane (soxhlet) and acetone (soxhlet). The resulting solid was dissolved in chloroform, filtered and precipitated into methanol. The resulting filtrate was dried under vacuum to afford 210 mg of product. GPC (THF) Mn (17,000 g/mol), Mw (20,000 g/mol). λ$_{max}$ 380 nm (solid film). $^1$H NMR gave the expected signals.

EXAMPLE 2

Polymer 9 has been synthesised according to Scheme 4 above.

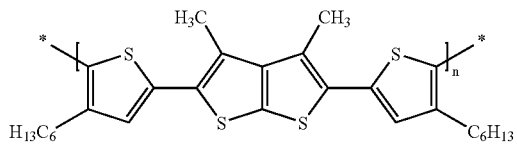

9

2,5-Bis(4-hexylthiophen-2-yl)-3,4-dimethylthieno[2,3-b]thiophene

To a solution of 2,5-dibromo-3,4-dimethylthieno[2,3-b]thiophene (3.02 g, 9.28 mmol) and sodium 4-hexylthiophene boronate (5.14 g, 20.4 mmol) in degassed DME (200 ml)

was added tetrakis(triphenyl-phosphine)palladium(0) (0.5 g, 5 mol %). The solution was heated to reflux and a saturated solution of sodium hyodrogen carbonate (4.2 g, 49 mmol) was added slowly. The reaction was refluxed for 16 h, cooled and diluted with diethyl ether. The layers were separated and the organics washed with 5% HCl, brine, dried ($Na_2SO_4$), filtered and concentrated under reduced pressure. The crude product was purified by column chromatography over silica (eluent: petrol) to afford the product after recrystallisation from petroi (1.03 g, 22%). :M/Z 500 ($M^+$). Found C, 66.9.1, H, 6.9, S, 25.3. Calc. for $C_{28}H_{36}S_4$ C, 67.2; H 7.2, S, 25.6. NMR gave the expected signals.

2,5-Bis(4-hexylthiophen-2-yl)-3,4-dimethylthieno[2,3-b]thiophene (9)

To a solution of 2,5-bis(4-hexylthiophen-2-yl)-3,4-dimethylthieno[2,3-b]thiophene (0.72 g, 1.45 mmol) in dry chloroform (20 ml) was added a solution of anhydrous ferric chloride (1.0 g, 6.2 mmol) in chloroform (110 ml) dropwise. A constant stream of nitrogen was passed through the solution to remove HCl formed during the reaction. The reaction was stirred for 18 h at 25° C., and then poured into methanol (500 ml). After stirring for 30 min the solution was filtered and washed with water and methanol. The resulting yellow solid was stirred in conc. ammonia solution for 1 h, filtered and dried. The solid was extracted with methanol (soxhlet), iso-hexane (soxhlet) and acetone (soxhlet). The resulting solid was dissolved in chloroform, filtered and precipitated into methanol. The resulting filtrate was dried under vacuum to afford 250 mg of product. GPC (THF) Mn (9,000 g/mol), Mw (22,000 g/mol). $\lambda_{max}$ 380 nm (solid film). $^1$H NMR gave the expected signals.

EXAMPLE 3

Polymer 10 was synthesised by Stille coupling as described below:

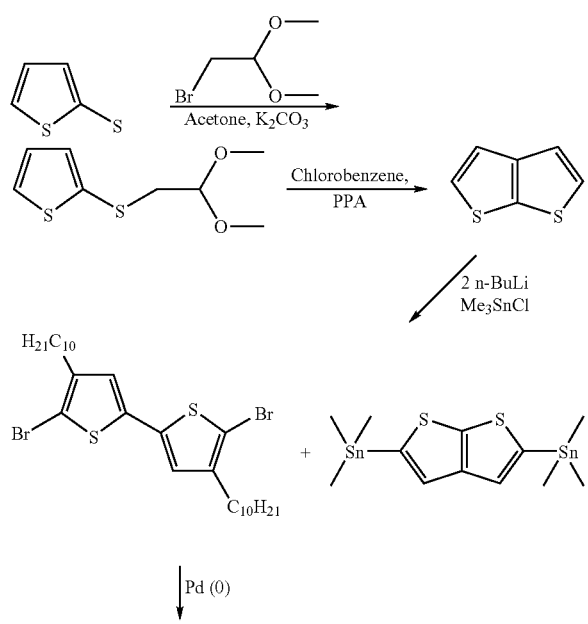

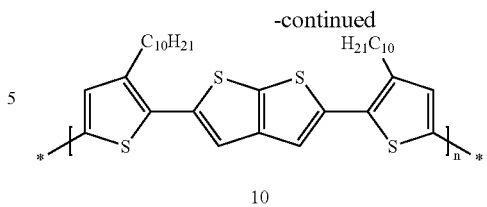

2-(2.2-Dimethoxyethylsulphanyl)-thiophene

To a solution of 2-thiophenethiol (12.3 g, 106 mmol) in acetone (180 ml), bromoacetaldehyde dimethyl acetal (13.6 ml, 115 mmol) was added, followed by potassium carbonate (21.8 g, 158 mmol). The reaction was refluxed for 16 h, cooled, then filtered and concentrated under reduced pressure. The crude product was purified by column chromatography over silica (eluent: petrol:DCM, 2:1) to afford the product as an orange oil (21.0 g, 97%). M/Z 204 ($M^+$). Found C, 47.0; H, 5.7; S, 32.3; O, 15.8. Calc. for $C_8H_{12}O_2S_2$ C, 47.0; H 5.9; S, 31.4; O, 15.7. $^1$H NMR (300 MHz, $CDCl_3$) δ 7.35 (dd, 1H, J=1.22 & 5.37 Hz), 7.17 (dd, 1H, J=1.22 & 3.58 Hz), 6.97 (dd, 1H, J=3.58 & 5.37 Hz), 4.51 (t,1 H, J=5.65 Hz), 3.35 (s, 6H), 2.98 (d, 2H, J=5.65 Hz).

Thieno[2,3-b]thiophene

A solution of 2-(2,2-dimethoxyethylsulphanyl)-thiophene (5.0 g, 24 mmol) in chlorobenzene (50 ml) was added dropwise over 5 minutes to a refluxing solution of 84% polyphosphoric acid (5 ml) in chlorobenzene (100 ml). The reaction mixture was refluxed for 18 h, cooled, poured into water, then extracted with DCM. The organics were washed with water, dried ($Na_2SO_4$), filtered and concentrated under reduced pressure. The crude product was purified by column chromatography over silica (eluent: petrol) to afford the product as a clear, pale yellow oil (1.53 g, 45%). M/Z 140 ($M^+$). Found C, 51.6; H, 2.8; S, 46.4. Calc. for $C_6H_4S_2$ C, 51.4; H 2.9; S, 45.7. $^1$H NMR (300 MHz, $CDCl_3$) δ 7.35 (d, 2H, J=5.09 Hz), 7.25 (d, 2H, J=5.09 Hz). $^{13}$C NMR (300 MHz, $CDCl_3$) δ 146.99, 137.28, 128.14, 119.75.

2,5-Bis-trimethylstannyl-thieno[2,3-b]thiophene

A solution of thieno[2,3-b]thiophene (2.81 g, 20 mmol) was dissolved in anhydrous THF (100 ml) and cooled to −78° C. under nitrogen. A solution of n-butyllithium (17.6 ml of a 2.5M solution in hexanes, 44 mmol) was added dropwise over 15 min, and the resulting solution was allowed to warm to RT and stirred at that temperature for 16 h. The resulting suspension was cooled to −78° C. and trimethyltin chloride (10.0 g, 50 mmol) was added at once as a solid. The reaction was allowed to warm to RT over 4 h and stirred at that temperature for an additional 20 h. The reaction was quenched by the addition of saturated sodium hydrogen carbonate (100 ml). Ethyl acetate (50 ml) was added and the layers separated. The organic layer was washed-with sodium carbonate (80 ml of a 2M aqeous solution) and brine (80 ml), dried (sodium sulfate), filtered and concentrated under reduced pressure. The resulting crude product was dry loaded onto a 20 g reverse phase silica column and eluted with acetonitrile. The first fraction was collected, concentrated and recrystallised from acetonitrile to afford the product as white flakes (4.15 g, 45%). M/Z cluster centred at 466 ($M^+$). Found C, 31.1; H, 4.4; S,13.8, Calc. for $C_{12}H_{20}S_2Sn_2$ C, 30.9; H, 4.3; S, 13.8. $^1$H NMR (300 MHz, $CDCl_3$) δ 7.23 (s, 2H), 0.38 (s,18H). $^{13}$C NMR (75 MHz, $CDCl_3$) δ 152.4, 147.7, 142.7, 126.3, −8.2.

5,5'-Dibromo-4,4'-bis(decyl)-2,2'-bithiophene 4,4'-Bis(decyl)-2,2'-bithiophene was prepared in analogy to the published procedure (see M. Zagorska and B. Krische *Polymer*, 1990, 31, p1379).

To a solution of 4,4'-bis(decyl)-2,2'-bithiophene (6.60 g, 14.8 mmol) in chloroform (100 ml) and glacial acetic acid (100 ml) at 5° C. in the dark was added N-bromosuccinimde (5.40 g, 30 mmol) portionwise over 1 h. The resulting solution was warmed to 20° C. and stirred for a further 16 h. The solvent was removed under reduced pressure and the residue suspended in MTBE (200 ml). Filtration of the solution removed succinimide byproduct. The filtrate was washed with 5% sodium carbonate (100 ml), water (100 ml) and brine (100 ml), dried (sodium sulfate), filtered and concentrated under reduced pressure. The resulting crude product was further purified by reverse phase column chromatography over RP18 silica (23 g) eluting with acetonitrile/THF 2:1. A final recrystallisation from ethyl acetate afforded the product (2.94 g, 33%). HRMS 602.1248 (calc. for $C_{28}H_{44}S_2Br^{79}{}_2$ 602.1251). $^1$H NMR (300 MHz, $CDCl_3$) δ 6.77 (s, 2H), 2.70 (t, 4H), 1.57 (quint, 4H), 1.28 (m, 28H), 0.88 (t, 6H). $^{13}$C NMR (75 MHz, $CDCl_3$) δ 143.0, 136.1, 124.5, 107.9, 31.9, 29.62, 29.57, 29.40, 29.35, 29.2, 22.7, 14.2.

Poly(2,5-bis(3-decylthiophen-2-yl)thieno[2,3-b]thiophene) (10)

A 10 ml glass vial was charged with a stirrer bar, 5,5'-dibromo-4,4'-didecylbithiophene (182 mg, 0.3 mmol), 2,5-bis(trimethylstannyl)-thieno[2,3-b]thiophene (140 mg, 0.3 mmol), tris(dibenzylideneacetone)dipalladium (0) (5.5 mg, 2 mol %), tri(o-tolyl)phosphine (14.6 mg, 16 mol %) and chlorobenzene (4.5 ml). The glass vial was purged with nitrogen and securely sealed. The glass vial was placed into a microwave reactor (Emrys Creator, Personal Chemistry Ltd) and heated to 200° C. A temperature ramp was used such that the vial was heated with stirring at 140° C. for 60 seconds, then 160° C. for 60 s, 180° C. for 60 s, and finally 200° C. for 10 minutes. Elapsed time was only calculated once the temperature had been reached. After cooling to RT, the reaction mixture was precipitated into a mixture of methanol (50 ml) and concentrated hydrochloric acid (2 ml) and and stirred for 16 h at 20° C. The precipitate was filtered and extracted with methanol (soxhlet) and acetone (soxhlet) for 12 h each. Finally the polymer was dissolved in warm chloroform, filtered and precipitated in petrol. The polymer was collected by centrifugation and dried under vacuum to afford the 105 mg of product. GPC ($CHCl_3$) Mn (15,000 g/mol), Mw (32,000 g/mol). $\lambda_{max}$ 465 nm (solid film). $^1$H NMR (300 MHz, CDCl3, 50° C.) δ 7.22 (s, 2H), 7.03 (s, 2H), 2.77 (t, 4H), 1.69 (quint, 4H), 1.4–1.20 (m, 28H), 0.88 (t, 6H).

EXAMPLE 4

Polymer 11 was synthesised by Stille coupling as described below:

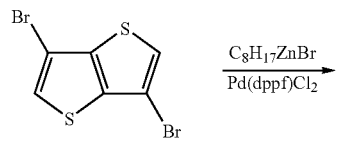

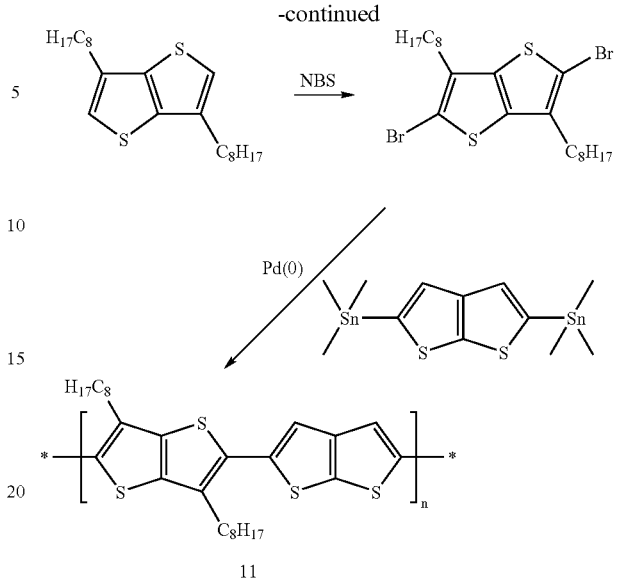

3,6-Dioctylthieno[3,2-b]thiophene

A 20 ml glass vial was charged with a stirrer bar, 3,6-dibromo-thieno[3,2-b]thiophene (see Fuller, L. S.; Iddon, B.; Smith, K. A. *J. Perkin Trans.* 1, 1997, p3465) (1.0 g, 3.35 mmol) and (1,1'-bis(diphenylphosphino)ferrocene) palladium (II) chloride (10 mg, 0.014 mmol). The glass vial was securely sealed and then purged with nitrogen. THF (2 ml) and octylzinc bromide (16.8 mL of a 0.5M solution in THF) were added, and the reaction stirred for 3 min at 25° C. The mixture was heated in a microwave reactor (Emrys Creator, Personal Chemistry Ltd) at 150° C. for 7 min. The reaction was cooled, diluted with MTBE (20 ml) and washed with 5% HCl (10 ml), water (3×10 ml), brine (10 m), dried (sodium sulfate), filtered and concentrated under reduced pressure. The crude material was further purified by filtration over silica (eluent: petrol), and the resulting waxy solid was recrystallised from ethanol to afford the product as a pale yellow solid (0.65 g, 54%). M/Z 364 (M$^+$). Found C, 72.3; H, 9.7,. Calc. for $C_{22}H_{36}S_2$ C, 72.5; H, 9.9. $^1$H NMR (300 MHz, $CDCl_3$) δ 8.95 (2H, s), 2.70 (4H, t), 1.74 (4H, quint), 1.31 (20H, m), 0.88 (6H, t). $^{13}$C NMR (75 MHz, $CDCl_3$) δ 139.3, 135.5, 120.8, 31.9, 29.8, 29.42, 29.37, 29.2, 28.8, 22.7, 14.1.

2,5-Dibromo-3,6-dioctylthieno[3,2-b]thiophene

To a solution of 3,6-dioctylthieno[3,2-b]thiophene (2.0 g, 5.5 mmol) in glacial acetic acid (50 ml) and chloroform (50 ml) at 5° C. was added N-bromosuccinimide (1.95 g, 11 mmol) portionwise over 1 h. The solution was stirred for a further 24 h at 20° C. The solvent was removed under reduced pressure, and the residue suspended in MTBE (100 ml) and filtered to remove succimide byproduct. The organic filtrate was washed with water (50 ml), 5% Na2CO3 (50 ml) and water (50 ml), dried (sodium sulfate), filtered and concentrated under reduced pressure. The residue was further purified by filtration thorugh silica (eluent: petrol) to afford a yellow oil that crystallised upon standing (2.379 g, 83%). HRMS 520.0472 (calc. for $C_{22}H_{34}S_2Br^{79}{}_2$ 520.0469). $^1$H NMR (300 MHz, $CDCl_3$) δ 2.66 (4H, t), 1.65 (4H, quint), 1.29 (20H, m), 0.87 (6H, t). ). $^{13}$C NMR (75 MHz, CDCl$_3$) δ 136.1, 134.4, 1.09.4, 31.9, 29.32, 29.27, 29.19, 28.1, 22.7, 14.1.

Poly(3,6-dioctylthieno[3,2-b]thiophene-co-thieno[2,3-b]thiophene) (11)

A 10 ml glass vial was charged with a stirrer bar, 2,5-dibromo-3,6-dioctylthieno[3,2-b]thiophene (157 mg, 0.3 mmol), 2,5-bis(trimethylstannyl)-thieno[2,3-b]thiophene (140 mg, 0.3 mmol), tris(dibenzylideneacetone)dipalladium (0) (5.5 mg, 2 mol %), tri(o-tolyl)phosphine (14.6 mg, 16 mol %) and chlorobenzene (6 ml). The glass vial was purged with nitrogen and securely sealed. The glass vial was placed into a microwave reactor (Emrys Creator, Personal Chemistry Ltd) and heated to 200° C. A temperature ramp was used such that the vial was heated with stirring at 140° C. for 60 seconds, then 160° C. for 60s, 180° C. for 60 s, and finally 200° C. for 10 minutes. Elapsed time was only calculated once the temperature had been reached. After cooling to RT, the reaction mixture was precipitated into a mixture of methanol (50 ml) and concentrated hydrochloric acid (2 ml) and stirred for 16 h at 20° C. The precipitate was filtered and extracted with methanol (soxhlet) and acetone (soxhlet) for 12 h each. Finally the polymer was dissolved in hot dichlorobenzene, filtered and precipitated in petrol. The polymer was collected by filtration and dried under vacuum to afford the 95 mg of product. GPC (CHCl$_3$) Mn (6,400 g/mol), Mw (9,400 g/mol). $\lambda_{max}$414 nm (solid film).

EXAMPLE 5

Polymer 12 was prepared by analogy to example 4.

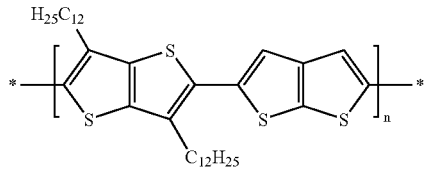

Poly(3,6-didodecyllthieno[3,2-b]thiophene-co-thieno[2,3-b]thiophene) (12)

A 10 ml glass vial was charged with a stirrer bar, 2,5-dibromo-3,6-didodecylthieno[3,2-b]thiophene (127 mg, 0.2 mmol), 2,5-bis(trimethylstannyl)-thieno[2,3-b]thiophene (93 mg, 0.2 mmol), tris(dibenzylideneacetone)dipalladium (0) (3.7 mg, 2 mol %), tri(o-tolyl)phosphine (6.0 mg, 8 mol %), lithium chloride (8.5 mg, 0.2 mmol) and chlorobenzene (5 ml). The glass vial was purged with nitrogen and securely sealed. The glass vial was placed into a microwave reactor (Emrys Creator, Personal Chemistry Ltd) and heated to 200° C. A temperature ramp was used such that the vial was heated with stirring at 140° C. for 60 seconds, then 160° C. for 60 s, 180° C. for 60 s, and finally 200° C. for 10 minutes. Elapsed time was only calculated once the temperature had been reached. After cooling to RT, the reaction mixture was precipitated into a mixture of methanol (50 ml) and concentrated hydrochloric acid (2 ml) and and stirred for 4 h at 20° C. The precipitate was filtered and extracted with acetone (soxhlet) and petrol (soxhlet) for 12 h each. Finally the polymer was dissolved in hot dichlorobenzene, filtered and precipitated in petrol. The polymer was collected by filtration and dried under vacuum to afford the 78 mg of product. GPC (CHCl$_3$) Mn (14,000 g/mol), Mw (22,0 00 g/mol). $\lambda_{max}$414 nm (solid film).

EXAMPLE 6

Polymer 13 has been synthesised according to Scheme 8 above.

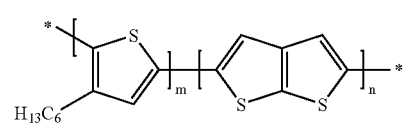

2,5-Diiodo-thieno[2,3-b]thiophene

A solution of thieno[2,3-b]thiophene (1.0 g, 7.1 mmol) in anhydrous tetrahydrofuran (40 ml), was cooled under nitrogen to −78° C., before adding n-butyl lithium, 2.5M in hexanes (6.8 ml) dropwise, and stirring at room temperature for 3 h. The reaction mixture was then cooled to −60° C., before adding iodine (3.6 g, 14 mmol), then stirring at room temperature for 18 h, with the exclusion of light. The reaction mixture was poured into water, extracted with DCM, washed with water, dried (Na$_2$SO$_4$), filtered and concentrated under reduced pressure. The crude product was purified by column chromatography over silica (eluent: petrol) to afford the product after recrystallisation from hot IMS as colourless platelet crystals (1.77 g, 63%). M/Z 392 (M$^+$). Found C, 18.5; H, 1.1; 1, 65.0; S, 15.6. Calc. for C$_6$H$_2$I$_2$S$_2$ C, 18.4; H, 0.5; I, 64.7; S, 16.4. $^1$H NMR (300 MHz, CDCl$_3$) δ 7.34 (s, 2H).

Poly(3-hexylthiophene-cothieno[2,3-b]thiophene)

To a solution of 2,5-dibromo-3-hexylthiophene (1.78 g, 5.45 mmol) and 2,5-diiodo-thieno[2,3-b]thiophene (0.24 g, 0.61 mmol) in anhydrous THF (28 ml) at 0° C. under nitrogen was added isopropylmagnesium chloride (3.3 ml of a 2.OM solution in THF, 6.6 mmol). The resulting solution was allowed to warm to room temperature and stirred for 4 h. [1,3-bis(diphenylphosphino)propane]-dichloronickel(II) (16 mg, 0.03 mmol) was added at once as a solid and the resulting mixture for stirred for 72 h at room temperature. The reaction was poured into methanol (180 ml) containing 37% HCl (20 ml) and stirred for 30 min. The precipitate was filtered and extracted successively with methanol (soxhlet), acetone (soxhlet) and iso-hexane (soxhlet). Finally the polymer was dissolved in chloroform and precipitated into methanol. The resulting precipitate was dried under vacuum to afform the product ( ). GPC (CHCl$_3$) Mn (13,000 g/mol), Mw (40,000 g/mol). $\lambda_{max}$462 nm (solid film).

EXAMPLE 7

Monomer 15 has been synthesised according to the following scheme:

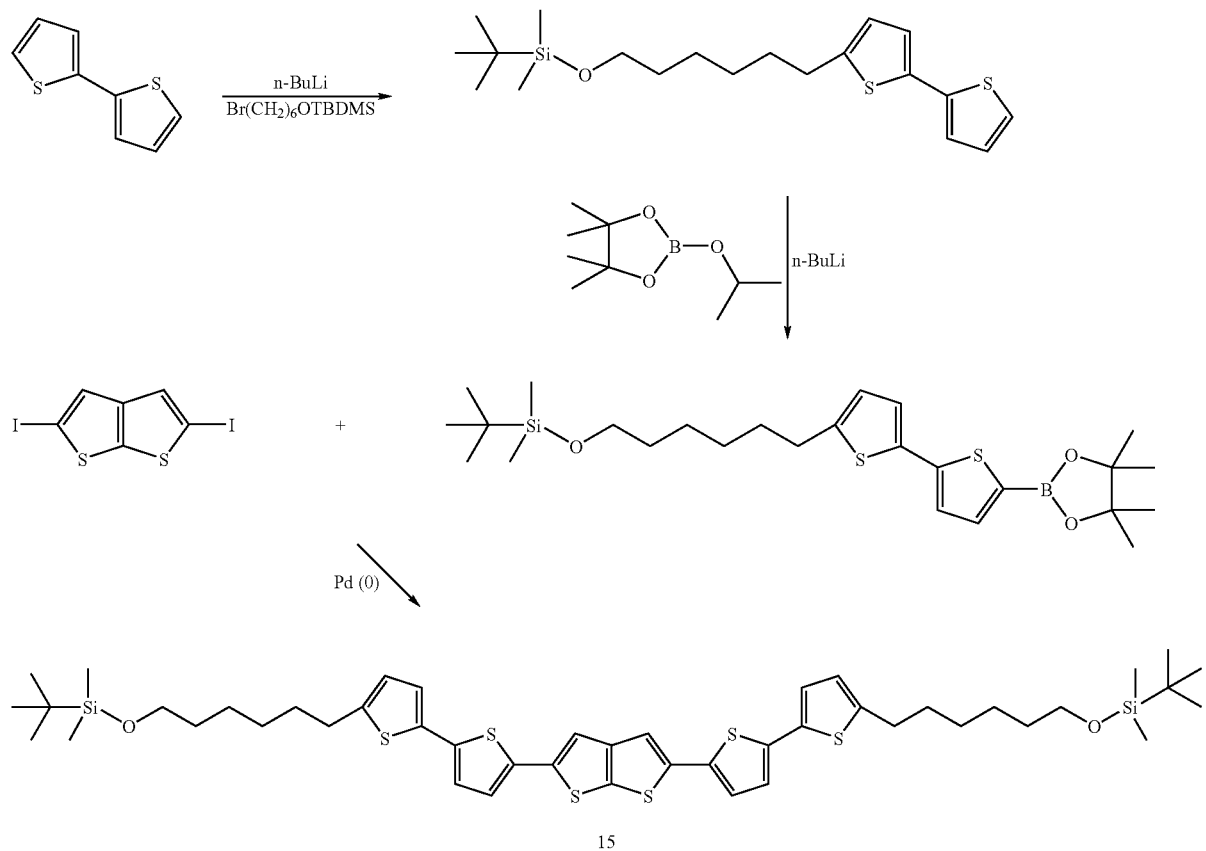

(6-[2.2'] Bithiophenyl-5-yl-hexyloxy)-tert-butyl-dimethylsilane

To a stirred solution of 2,2'-bithiophene (10.0 g, 60.24 mmol) in dry THF (150 ml) was added n-butyllithium (2.5 M in hexanes, 20.0 ml, 50.0 mmol) dropwise at −78° C. under nitrogen. After complete addition, the mixture was allowed to warm to room temperature, with stirring, over 2 h, followed by the addition of 6-bromohexyloxy-tert-butyi-dimethylsilane (14.75 g, 50.0 mmol). The resultant mixture was stirred overnight at room temperature. The reaction was quenched with sat. aq. ammonium chloride, and the reaction mixture was extracted with ethyl acetate (3×70 ml). The combined organic extracts were washed with water, brine, and dried over magnesium sulphate. The solvent was removed under reduced pressure and the residue was purified by column chromatography (silica gel, petroleum/ethyl acetate from 100:0 to 20:1), to afford the product as a pale green oil (15.07 g, 79%). $^1$H NMR (300 MHz, CDCl$_3$): δ (ppm) 7.08 (m, 1H, Ar—H), 7.03,(m, 1H, Ar—H), 6.92 (m, 2H, Ar—H), 6.61 (d, J=3.6 Hz, 1 H, Ar—H), 3.55 (t, J=6:2 Hz, 2H, OCH$_2$), 3.34 (t, J=6.8 Hz, 2H, ArCH$_2$), 1.25–1.85 (m, 8H, CH$_2$), 0.86 (s, 9H, CH$_3$), 0.01 (s, 6H, CH$_3$); $^{13}$C NMR (75 MHz, CDCl$_3$): δ (ppm).145.1 (quat.), 138.0 (quat.), 134.8 (quat.), 127.6 (CH), 124.7 (CH), 123.7 (CH), 123.4. (CH), 122.9 (CH), 63.0 (OCH$_2$), 33.8 (CH$_2$), 32.9 (CH$_2$), 32.7 (CH$_2$), 28.0 (CH$_2$), 26.0 (CH$_3$) 25.1 (CH$_2$), 18.4 (quat.), −5.2 (CH$_3$); MS (m/e): 380 (M$^+$, 27%), 323 (63), 179 (100), 75 (37).

2-{5'-[6-(tert-Butyl-dimethyl-silanyloxy)-hexyl]-[2,2']bithiophenyl-5-yl}-4,4,5,5-tetramethyl-[1,3,2]di-oxaborolane To an ice-cooled solution of (6-[2,2']bithiophenyl-5-yl-hexyloxy)-tert-butyl-dimethylsilane (10 g, 19.76 mmol) in anhydrous THF (150 ml) was added dropwise a solution of n-butyllithium (2.5 M in hexanes, 7.91 ml, 19.76 mmol) under nitrogen, with stirring. After 2 h, pinacol boronate (4.04 g, 21.72 mmol) was added. The ice bath was removed, and the resultant mixture was stirred overnight at room temperature. The reaction was quenched with the addition of saturated aqueous NH$_4$Cl and the mixture extracted with ethyl acetate (3×70 ml). The combined organic extracts were washed with brine, dried over magnesium sulphate, and evaporated under reduced pressure. The residue was purified by column chromatography on silica, eluting with petroleum ether/ethyl (9:1), to give the product as a blue oil (9.52 g, 72%). $^1$H NMR (300 MHz, CDCl$_3$): δ (ppm) 7.46 (d, J=3.6 Hz, 1 H, Ar—H), 7.10 (d, J=3.6 Hz, 1H, Ar—H), 6.99 (d, J=3.4 Hz, 1H, Ar—H), 6.62 (d, J=3.4 Hz, 1H, Ar—H), 3.56 (t, J=6.4 Hz, 2H, OCH$_2$), 2.73 (t, J=7.4 Hz, 2H, ArCH$_2$), 1.21–1.70 (m, 20H, CH$_2$ and CH$_3$), 0.86 (s, 9H, CH$_3$), 0.01 (s, 6H, CH$_3$); $^{13}$C NMR (75 MHz, CDCl$_3$): δ (ppm) 145.9 (2×quat.), 144.8 (quat.), 138.0 (CH.), 134.7 (quat.), 125.0 (CH), 124.2 (CH); 124.1 (CH), 84.1 (quat.), 63.2 (OCH$_2$), 32.8 (CH$_2$), 31.6 (CH$_2$), 30.2 (CH$_2$), 28.9 (CH$_2$), 26.0 (CH$_3$) 25.6 (CH$_2$), 24.8 (CH$_3$),18.4 (quat.), −5.2 (CH$_3$); MS (m/e): 506 (M+, 32%), 331 (31), 305 (31), 279 (100), 261 (32), 205 (51), 83 (71).

2,5-Bis-{5'-[6-(tert-butyldimethylsilanyloxy)-hexyl]-[2,2']bithiophenyl-5-yl}-thieno[2,3-b]thiophene Tetrakis(triphenylphosphine)palladium(0.05 g) was added to a solution of 2,5-diiodothioeno[2,3-b]thiophene (0.10 g, 0.26 mmol) in dry THF, with stirring, under nitrogen. After 20 min, 2-{5'-[6-(tert-butyldimethylsilanyloxy)hexyl]-[2,2']bithiophenyl-5-yl}-4,4,5,5-tetramethyl[1,3,2]dioxaborolane (0.41 g, 0.80 mmmol) and a solution of potassium carbonate (0.22 g, 1.60 mmol) in water (5 ml) was added. The resultant mixture was heated at reflux for 1.5 h. After cooling, water (50 ml) was added and the precipitate filtered off, washed with water and diethyl ether, to give a yellow solid (0.20 g, 87%). $\lambda_{MAX}$(CHCl$_3$) 395 nm; $^1$H NMR (300 MHz, CDCl$_3$): δ (ppm) 7.21 (s, 2H, Ar—H), 7.06 (d, J=3.8 Hz, 2H, Ar—H), 6.99 (m, 4H, Ar—H), 6.68 (d, J=3.6 Hz, 2H, Ar—H); 3.61 (t, J=6.4 Hz, 4H, OCH$_2$), 2.80 (t, J=7.3 Hz 4H, ArCH$_2$), 1.31–1.68 (m, 16H, CH$_2$), 0.90 (s, 18H, CH$_3$); 0.05 (s, 12H, CH$_3$). $^{13}$C NMR (75 MHz, CDCl$_3$): δ (ppm) 146.2, 145.7, 139.9, 137.3, 135.5, 135.0, 134.4, 124.8, 124.5, 123.6, 123.5, 116.0, 63.1, 32.7, 31.5, 30.1, 28.8, 25.9, 25.5, 18.3, −4.3.

Use Example A

A comparison of the optical properties of polymers 8, 10, 11, & 13 according to the examples 1, 3, 4 and 6 with the fully conjugated thiophene co-polymer 14 of prior art was made.

14

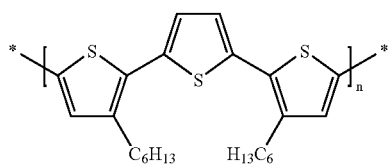

Figure 2:
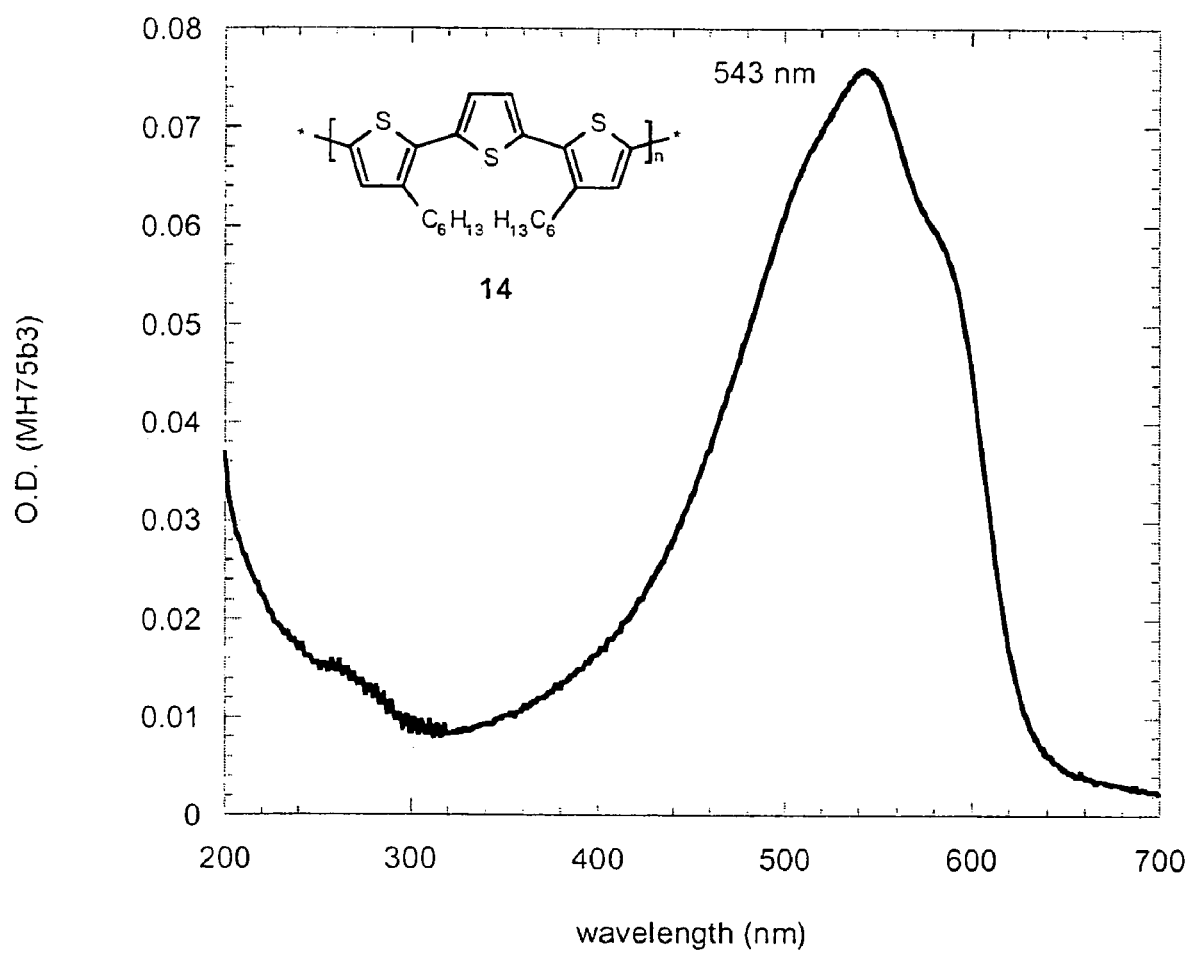
FIG. 2 shows the UV spectrum of a polymer according to prior art.

FIGS. 1 and 2 show the UV spectra of polymer films cast from solution of polymers 8, 10, 11 & 13 (FIG. 1) and 14 (FIG. 2). It is immediately apparent that the maximum absorbance of the thieno[2,3-b]thiophene containing polymers 8, 10, 11, 13 are all blue shifted in comparison to the thiophene only polymer 14 (up to 160 nm). Furthermore, polymer 8 has a blue solid-state photoluminescence in comparison to orange for polymer 10.

Use Example B—Transistor Fabrication and Measurement

Thin-film organic field-effect transistors (OFETs) were fabricated on highly doped silicon substrates with thermally grown silicon oxide (SiO$_2$) insulating layer, where the substrate served as a common gate electrode. Transistor source-drain gold electrodes were photolithographically defined on the SiO$_2$ layer. Prior to organic semiconductor deposition, FET substrates were treated with a silylating agent hexamethyldisilazane (HMDS). Thin semiconductor films were then deposited by spin-coating polymer solutions in chloroform or xylene (0.4–1 wt %) on FET substrates. The electrical characterization of the transistor devices, was carried out under ambient atmosphere using computer controlled Agilent 4155C Semiconductor Parameter Analyser.

Transistor characteristics for examples 10 and 12 were measured on films prepared by spin coating. The results are shown in table 1. The films were heated to 100° C. for 10 min under nitrogen to remove residual solvent, and then cooled to room temperature to measure the transistor characteristics.

Figure 3A:
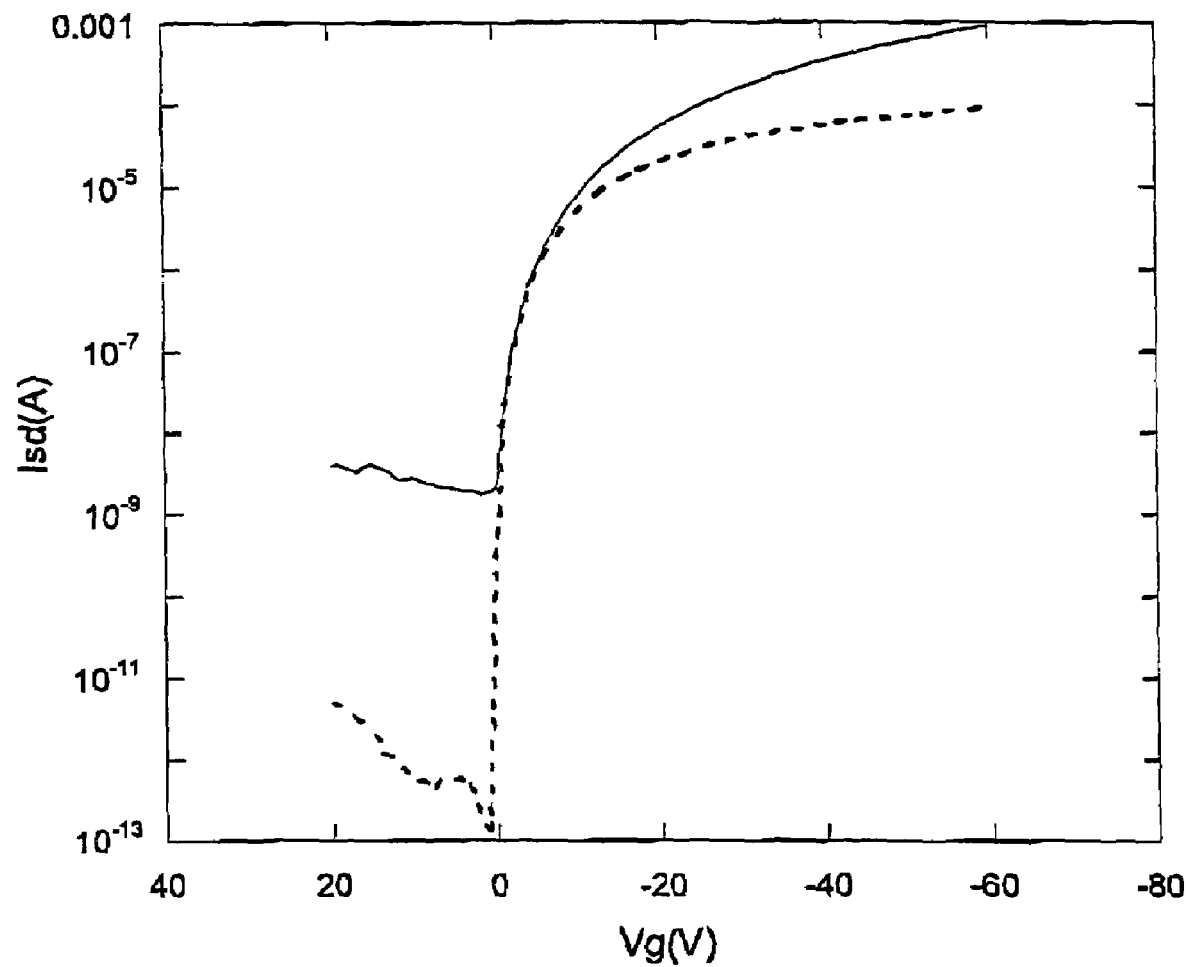
FIGS. 3a and 3b show the transfer and output characteristics, respectively, of an OFET comprising a polymer according to the present invention.
Figure 3B:
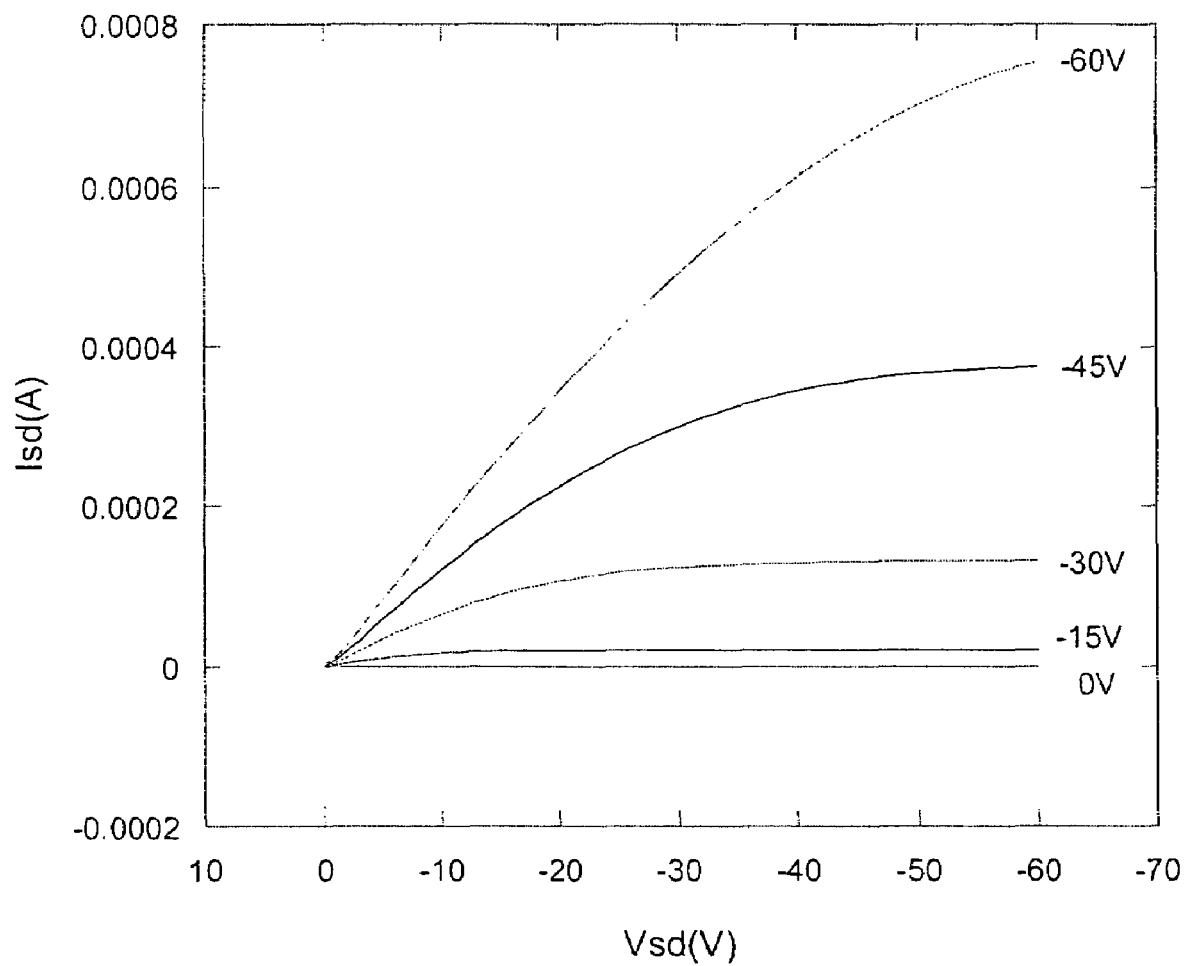

FIGS. 3a and 3b show the transfer and output characteristics for compound 10 of example 3. Depicted is the current (I)–voltage (V) characteristics in a transistor device with 10 micron channel length and 20,000 micron channel width. FIG. 3a shows the transfer curves. The transistor gate voltage ($V_g$) is varied between 20 and −60 volts for two different setting of Source-Drain voltage ($V_{sd}$). The transistor Source-Drain current $I_{sd}$ is plotted versus $V_g$ for $V_{sd}$=−5 (dotted line) and −60 V (solid line), respectively. FIG. 3b shows the output curves. The Source-Drain voltage ($V_{sd}$) is varied between 0 and −60 volts with a different bias voltage applied to the gate electrode ($V_g$). The transistor Source - Drain current ($I_{sd}$) is plotted versus $V_{sd}$ for $V_g$=0, −15, −30, −45 and −60 V, respectively.

The devices showed typical p-type behaviour with good current modulation, and well-defined linear and saturation regimes. Field effect mobility was calculated in the saturation regime ($V_d$>($V_g$−$V_0$)) using equation (1)

$$\left(\frac{dI_d^{sat}}{dV_g}\right)_{V_d} = \frac{WC_i}{L}\mu^{sat}(V_g - V_0) \tag{1}$$

wherein W is the channel width, L the channel length, $C_i$ the capacitance of insulating layer, $V_g$ the gate voltage, $V_d$ the drain voltage, $I_d$ the drain current, $V_0$ the turn-on voltage and $\mu^{sat}$ is the saturated charge carrier mobility. The turn-on voltage ($V_0$) was determined as the onset of source-drain current (FIG. 3).

Materials 10 and 12 demonstrated good air stability, as exemplified by the high on/off ratios for measurements in air (table 1). The device characteristics showed little change after testing following storage in air.

TABLE 1

| Material | Initial Saturated Mobility | On/off ratio |
|---|---|---|
| 10 | 1.7 × 10$^{-2}$ cm$^2$/vs | 1 × 10$^6$ |
| 12 | 3 × 10$^{-3}$ cm$^2$/vs | 2 × 10$^6$ |

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

In the foregoing and in the examples, all temperatures are set forth uncorrected in degrees Celsius and, all parts and percentages are by weight, unless otherwise indicated.

The entire disclosures of all applications, patents and publications, cited herein and of corresponding European application No. 03019501.0, filed Aug. 28, 2003 are incorporated by reference herein.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

The invention claimed is:

1. A monomer, oligomer or polymer of formula I

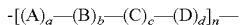   I wherein
A and C are, independently of each other in each case, a group of formula II

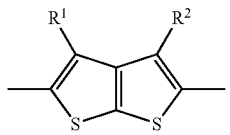   II $R^1$ and $R^2$ are, independently of each other, H, halogen, or a straight chain, branched or cyclic alkyl with 1 to 20 C-atoms, which is unsubstituted, mono- or poly-substituted by F, Cl, Br, I, OH or CN, in which one or more non-adjacent $CH_2$ groups are optionally replaced, in each case independently from one another, by —O—, —S—, —NH—, —$NR^0$—, —$SiR^0R^{00}$—, —CO—, —COO—, —OCO—, —OCO—O—, —S—CO—, —CO—S—, —CH=CH— or —C≡C— in such a manner that O and/or S atoms are not linked directly to one another, or are optionally substituted aryl or heteroaryl, P—Sp—or P—Sp*—, P is a polymerisable or reactive group, P* is a group that can be converted to or substituted by a polymerisable or reactive group P, Sp is a spacer group or a single bond, $R^0$ and $R^{00}$ are, independently of each other, H, aryl or alkyl with 1 to 12 C-atoms, B and D are, independently of each other in each case, —$CX^1$=$CX^2$—, —C≡C— or an arylene or heteroarylene group that is optionally substituted with one or more $R^1$ groups, $X^1$ and $X^2$ are, independently of each other, H, F, Cl or CN, a, b, c, d are, independently of each other, 0 or an integer of 1 to 10, with a+b+c+d>0, and wherein in at least one recurring unit $[(A)_a—(B)_b—(C)_c—(D)_d]$ at least one of a and c is 1 and at least one of b and d is 1, and n is an integer $\geq 1$, wherein the recurring units $[(A)_a—(B)_b—(C)_c—(D)_d]$ are identical or different, and with the proviso that if a is 1, then —$(B)_b—(C)_c—(D)_d$— is different from —CH=CH—Ar—CH=CH—, with Ar being 2,5-thiophene, 1,4-phenylene or 2,5-dimethoxy-1,4-phenylene, or the compounds comprise at least one group P—Sp—or P*—Sp—.

2. A monomer, oligomer or polymer according to claim 1, wherein the monomer, oligomer or polymer of formula I is of formula I1

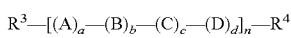   I1 wherein A, B, C, D, a, b, c and d are defined as in claim 1, and $R^3$ and $R^4$ are, independently of each other, H, halogen, $Sn(R^0)_3$, $CH_2Cl$, COH, CH=$CH_2$, $SiR^0R^{00}R^{000}$, optionally substituted aryl or heteroaryl, P—Sp—or P*—Sp—, wherein P, P*, Sp, $R^0$ and $R^{00}$ are defined as in claim 1, and $R^{000}$ has one of the meanings of $R^0$.

3. An oligomer or polymer according to claim 1, having a degree of polymerisation of 10 to 5000.

4. A monomer according to claim 2, wherein n is 1 and one or both of $R^3$ and $R^4$ are P—Sp—or P*—Sp—.

5. A monomer, oligomer or polymer according to claim 1, wherein $R^1$ and $R^2$ are, independently of each other, $C_1$–$C_{20}$-alkyl that is optionally substituted with one or more fluorine atoms, $C_1$–$C_{20}$-alkoxy, $C_1$–$C_{20}$-alkenyl, $C_1$–$C_{20}$-alkynyl, $C_1$–$C_{20}$-thioether, $C_1$–$C_{20}$-silyl, $C_1$–$C_{20}$-ester, $C_1$–$C_{20}$-amino, $C_1$–$C_{20}$-fluoroalkyl or optionally substituted aryl or heteroaryl.

6. A monomer, oligomer or polymer according to claim 1, wherein

B and/or D are, independently of each other, 1,4-phenylene, fluorinated 1,4-phenylene, 2,5-pyridine, 2,5-pyrimidine, p,p'-biphenyl, naphthalene-2,6-diyl, thiophene-2,5-diyl, fluorinated or alkylated thiophene-2,5-diyl, fluorinated benzo[1,2-b:4,5-b']dithiophene, 2,5-thiazole, 2,5-thiadiazole, 2,5-oxazole or 2,5-oxadiazole, all of which are unsubstituted, mono- or polysubstituted with L, wherein L is F, Cl, Br, or an alkyl, alkoxy, alkylcarbonyl or alkoxycarbonyl group with 1 to 20 C atoms, wherein one or more H atoms are optionally replaced by F or Cl, or is $C_1$–$C_{20}$-alkenyl, $C_1$–$C_{20}$-alkynyl, $C_1$–$C_{20}$-thioalkyl, $C_1$–$C_{20}$-silyl, $C_1$–$C_{20}$-ester, $C_1$–$C_{20}$-amino, or $C_1$–$C_{20}$-fluoroalkyl.

7. A monomer, oligomer or polymer according to claim 1, wherein B and/or D are, independently of each other, thiophene-2,5-diyl or 2.2-dithiophene, that are optionally substituted by one or more groups having the meaning of $R^1$ in claim 1, or a group of formula III

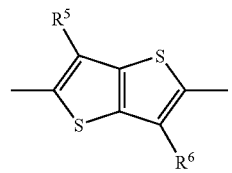   III wherein $R^5$ and $R^6$ have one of the meanings of $R^1$.

8. A monomer, oligomer or polymer according to claim 1, which is selected from the following formulae

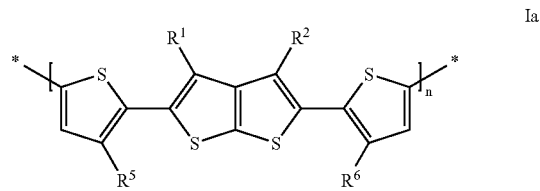   Ia

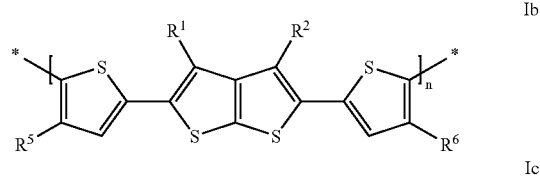   Ib

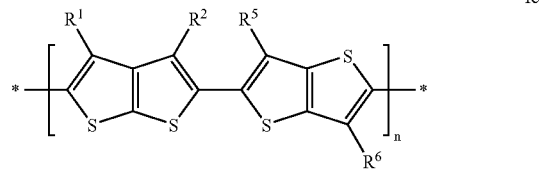   Ic wherein R¹, R² and n are defined as in claim 1 and R⁵ and R⁶ have one of the meanings of R¹.

9. A monomer according to claim 1, which is selected from the following formulae wherein R¹, R² and Sp are defined as in claim 1, P' is defined as P or P* in claim 1, and R' is H, halogen, Sn(R⁰)₃, CH₂Cl, COH, CH=CH₂ SiR⁰R⁰⁰R⁰⁰⁰, optionally substituted aryl or heterbaryl, P—Sp— or P*—Sp—, wherein P, P*, Sp, R⁰ and R⁰⁰ are defined as in claim 1, and R⁰⁰⁰ having one of the meanings of R⁰.

10. A polymerisable liquid crystal material comprising one or more monomer, oligomer or polymer according to claim 1 comprising at least one polymerisable group, and optionally comprising one or more polymerisable compounds not of claim 1, wherein at least one of the polymerisable compounds is mesogenic or liquid crystalline.

11. An anisotropic polymer film with charge transport properties obtainable from a polymerisable liquid crystal material according to claim 10 that is aligned in its liquid crystal phase into macroscopically uniform orientation and polymerised or crosslinked to fix the oriented state.

12. A side chain liquid crystal polymer obtained by
I) polymerisation of one or more
a) monomer or oligomer according to claim 1 or
b) a polymerisable liquid crystal material comprising one or more monomer, oligomer or polymer according to claim 1 comprising at least one polymerisable group, and optionally comprising one or more polymerisable compounds not of claim 1, wherein at least one of the polymerisable compounds is mesogenic or liquid crystalline,
or
II) grafting to a polymer backbone in a polymeranalogous reaction, optionally with one or more mesogenic or non-mesogenic comonomers that are not of claim 1, one or more
a) monomer or oligomer according to claim 1, or
b) a polymerisable liquid crystal material comprising one or more monomer, oligomer or polymer according to claim 1 comprising at least one polymerisable group, and optionally comprising one or more polymerisable compounds not of claim 1, wherein at least one of the polymerisable compounds is mesogenic or liquid crystalline.

13. A semiconductor or charge transport material in an optical, electrooptical or electronic device, a field effect transistor (FET), an integrated circuitry, a thin film transistor (TFT) for flat panel display applications, or a radio frequency identification (RFID) tag, or a semiconducting component for organic light emitting diode (OLED) applications, a charge transport or electroluminescent layer in an electroluminescent display or backlight of a liquid crystal display (LCD), comprising
a monomer, oligomer or polymer of claim 1,
a polymerisable liquid crystal material comprising one or more monomer, oligomer or polymer according to claim 1 comprising at least one polymerisable group, and optionally comprising one or more polymerisable compounds not of claim 1, wherein at least one of the polymerisable compounds is mesogenic or liquid crystalline,
an anisotropic polymer film with charge transport properties obtainable from a polymerisable liquid crystal material described above that is aligned in its liquid crystal phase into macroscopically uniform orientation and polymerised or
crosslinked to fix the oriented state, or
a side chain liquid crystal polymer obtained by
I) polymerisation of one or more
a) monomer or oligomer according to claim 1 or
b) a polymerisable liquid crystal material comprising one, or more monomer, oligomer or polymer according to claim 1 comprising at least one polymerisable group, and optionally comprising one or more polymerisable compounds not of claim 1, wherein at least one of the polymerisable compounds is mesogenic or liquid crystalline,
or
II) grafting to a polymer backbone in a polymeranalogous reaction, optionally with one or more mesogenic or non-mesogenic comonomers that are not of claim 1, one or more
a) monomer or oligomer according to claim 1, or
b) a polymerisable liquid crystal material comprising one or more monomer, oligomer or polymer according to claim 1 comprising at least one polymerisable group, and optionally comprising one or more polymerisable compounds not of claim 1, wherein at least one of-the polymerisable compounds is mesogenic or liquid crystalline.

14. An electroluminescent material, a photovoltaic or sensor device, an electrode material in a battery, a photoconductor, an electrophotographic device, an electrophotographic recording or an alignment layer in a LCD or OLED device comprising
a monomer, oligomer or polymer of claim 1,
a polymerisable liquid crystal material comprising one or more monomer, oligomer or polymer according to claim 1 comprising at least one polymerisable group, and optionally comprising one or more polymerisable compounds not of claim 1, wherein at least one of the polymerisable compounds is mesogenic or liquid crystalline,
an anisotropic polymer film with charge transport properties obtainable from a polymerisable liquid crystal material described above that is aligned in its liquid crystal phase into macroscopically uniform orientation and polymerised or crosslinked to fix the oriented state,
or
a side chain liquid crystal polymer obtained by
I) polymerisation of one or more
a) monomer or oligomer according to claim 1 or
b) a polymerisable liquid crystal material comprising one or more monomer, oligomer or polymer according to claim 1 comprising at least one polymerisable group, and optionally comprising one or more polymerisable compounds not of claim 1, wherein at least one of the polymerisable compounds is mesogenic or liquid crystalline,
or
II) grafting to a polymer backbone in a polymeranalogous reaction, optionally with one or more-mesogenic or non-mesogenic comonomers that are not of claim 1, one or more
a) monomer or oligomer according to claim 1, or
b) a polymerisable liquid crystal material comprising one or more monomer, oligomer or polymer according to claim 1 comprising at least one polymerisable group, and optionally comprising one or more pblymerisable compounds not of claim 1, wherein at least one of the polymerisable compounds is mesogenic or liquid crystalline.

15. An optical, electrooptical or electronic device, FET, integrated circuit (IC), TFT, OLED or alignment layer comprising
a monomer, oligomer or polymer of claim 1,
a polymerisable liquid crystal material comprising one or more monomer, oligomer or polymer according to claim 1 comprising at least one polymerisable group, and optionally comprising one or more polymerisable compounds not of claim 1, wherein at least one of the polymerisable-compounds is mesogenic or liquid crystalline, an anisotropic polymer film with charge transport properties obtainable from a polymerisable liquid crystal material described above that is aligned in its liquid crystal phase into macroscopically uniform orientation and polymerised or crosslinked to fix the oriented state, or a side chain liquid crystal polymer obtained by I) polymerisation of one or more a) monomer or oligomer according to claim 1 or b) a polymerisable liquid crystal material comprising one or more monomer, oligomer or polymer according to claim 1 comprising at least one polymerisable group, and optionally comprising one or more polymerisable compounds not of claim 1, wherein at least one of the polymerisable compounds is mesogenic or liquid crystalline, or II) grafting to a polymer backbone in a polymeranalogous reaction, optionally with one or more mesogenic or non-mesogenic comonomers that are not of claim 1, one or more a) monomer or oligomer according to claim 1, or b) a polymerisable liquid crystal material comprising one or more monomer, oligomer or polymer according to claim 1 comprising at least one polymerisable group, and optionally comprising one or more polymerisable compounds not of claim 1, wherein at least one of the polymerisable compounds is mesogenic or liquid crystalline.

16. A TFT or TFT array for a flat panel display, radio frequency identification (RFID) tag, electroluminescent display or backlight, comprising a monomer, oligomer or polymer of claim 1, a polymerisable liquid crystal material comprising one or more monomer, oligomer or polymer according to claim 1 comprising at least one polymerisable group, and optionally comprising one or more polymerisable compounds not of claim 1, wherein at least one of the polymerisable compounds is mesogenic or liquid crystalline, an anisotropic polymer film with charge transport properties obtainable from a polymerisable liquid crystal material described above that is aligned in its liquid crystal phase into macroscopically uniform orientation and polymerised or crosslinked to fix the oriented state, or a side chain liquid crystal polymer obtained by I) polymerisation of one or more a) monomer or oligomer according to claim 1 or b) a polymerisable liquid crystal material comprising one or more monomer, oligomer or polymer according to claim 1 comprising at least one polymerisable group, and optionally comprising one or more polymerisable compounds not of claim 1, wherein at least one of the polymerisable compounds is mesogenic or liquid crystalline, or II) grafting to a polymer backbone in a polymeranalogous reaction, optionally-with one or more mesogenic or non-mesogenic comonomers that are not of claim 1, one or more a) monomer or oligomer according to claim 1, or b) a polymerisable liquid crystal material comprising one or more monomer, oligomer or polymer according to claim 1 comprising at least one polymerisable group, and optionally comprising one or more polymerisable compounds not of claim 1, wherein at least one of the polymerisable compounds is mesogenic or liquid crystalline.

17. A security marking or device comprising a FET or an RFID tag a monomer, oligomer or polymer of claim 1, a polymerisable liquid crystal material comprising one or more monomer, oligomer or polymer according to claim 1 comprising at least one polymerisable group, and optionally comprising one or more polymerisable compounds not of claim 1, wherein at least one of the polymerisable compounds is mesogenic or liquid crystalline, an anisotropic polymer film with charge transport properties obtainable from a polymerisable liquid crystal material described above that is aligned in its liquid crystal phase into macroscopically uniform orientation and polymerised or crosslinked to fix the oriented state, or a side chain liquid crystal polymer obtained by I) polymerisation of one or more a) monomer or oligomer according to claim 1 or b) a polymerisable liquid crystal material comprising one or more monomer, oligomer or polymer according to claim 1 comprising at least one polymerisable group, and optionally comprising one or more polymerisable compounds not of claim 1, wherein at least one of the polymerisable compounds is mesogenic or liquid crystalline, or II) grafting to a polymer backbone in a polymeranalogous reaction, optionally with one or more mesogenic or non-mesogenic comonomers that are not of claim 1, one or more a) monomer or oligomer according to claim 1, or b) a polymerisable liquid crystal material comprising one or more monomer, oligomer or polymer according to claim 1 comprising at least one polymerisable group, and optionally comprising one or more polymerisable compounds not of claim 1, wherein at least one of the polymerisable compounds is mesogenic or liquid crystalline.

18. A conducting ionic material that is an oxidatively or reductively doped monomer, oligomer or polymer of claim 1, a polymerisable liquid crystal material comprising one or more monomer, oligomer or polymer according to claim 1 comprising at least one polymerisable group, and optionally comprising one or more polymerisable compounds not of claim 1, wherein at least one of the polymerisable compounds is mesogenic or liquid crystalline, an anisotropic polymer film with charge transport properties obtainable from a polymerisable liquid crystal material described above that is aligned in its liquid crystal phase into macroscopically uniform orientation and polymerised or crosslinked to fix the oriented state, or a side chain liquid crystal polymer obtained by I) polymerisation of one or more a) monomer or oligomer according to claim 1 or b) a polymerisable liquid crystal material comprising one or more monomer, oligomer or polymer according to claim 1 comprising at least one polymerisable group, and optionally comprising one or more polymerisable compounds not of claim 1, wherein at least one of the polymerisable compounds is mesogenic or liquid crystalline, or II) grafting to a polymer backbone in a polymeranalogous reaction, optionally with one or more mesogenic or non-mesogenic comonomers that are not of claim 1, one or more a) monomer or oligomer according to claim 1, or b) a polymerisable liquid crystal material comprising one or more monomer, oligomer or polymer according to claim 1 comprising at least one polymerisable group, and optionally comprising one or more polymerisable compounds not of claim 1, wherein at least one of the polymerisable compounds is mesogenic or liquid crystalline.

19. A charge injection layer, planarising layer, antistatic film or conducting substrate or pattern for electronic applications or flat panel display, comprising a monomer, oligomer or polymer of claim 1, a polymerisable liquid crystal material comprising one or more monomer, oligomer or polymer according to claim 1 comprising at least one polymerisable group, and optionally comprising one or more polymerisable compounds not of claim 1, wherein at least one of the polymerisable compounds is mesogenic or liquid crystalline, an anisotropic polymer film with charge transport properties obtainable from a polymerisable liquid crystal material described above that is aligned in its liquid crystal phase into macroscopically uniform orientation and polymerised or crosslinked to fix the oriented state, or a side chain liquid crystal polymer obtained by I) polymerisation of one or more a) monomer or oligomer according to claim 1 or b) a polymerisable liquid crystal material comprising one or more monomer, oligomer or polymer according to claim 1 comprising at least one polymerisable group, and optionally comprising one or more polymerisable compounds not of claim 1, wherein at least one of the polymerisable compounds is mesogenic or liquid crystalline, or II) grafting to a polymer backbone in a polymeranalogous reaction, optionally with one or more mesogenic or non-mesogenic comonomers that are not of claim 1, one or more a) monomer or oligomer according to claim 1, or b) a polymerisable liquid crystal material comprising one or more monomer, oligomer or polymer according to claim 1 comprising at least one pblymerisable group, and optionally comprising one or more polymerisable compounds not of claim 1, wherein at least one of the polymerisable compounds is mesogenic or liquid crystalline.

20. A monomer, oligomer or polymer according to claim 6, wherein L is $C_1$–$C_{20}$-alkyl or $C_1$–$C_{20}$-fluoroalkyl.

* * * * *

UNITED STATES PATENT AND TRADEMARK OFFICE
CERTIFICATE OF CORRECTION

PATENT NO.       : 7,183,418 B2
APPLICATION NO.  : 10/928724
DATED            : February 27, 2007
INVENTOR(S)      : Martin Heeney It is certified that error appears in the above-identified patent and that said Letters Patent is hereby corrected as shown below:

Column 35, line 25, reads "P-Sp-or" should read -- P-Sp- or --
Column 35, line 50, reads "P-Sp-or" should read -- P-Sp- or --
Column 35, line 61, reads "P-Sp-or" should read -- P-Sp- or --
Column 35, line 67, reads "P-Sp-or" should read -- P-Sp- or --
Column 38, in formula Io reads "

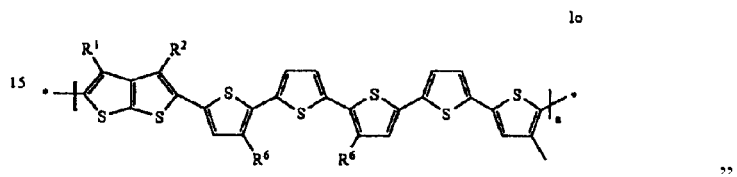

"

should read --

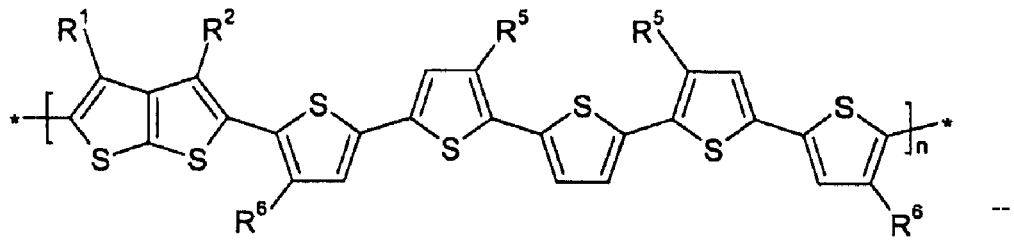

--

Column 39, line 3, reads "$CH=CH_2$ $SiR^0R^{00}R^{000}$," should read
-- $CH=CH_2$, $SiR^0R^{00}R^{000}$, --
Column 39, line 4, reads "heterbaryl, P-Sp-or" should read -- heteroaryl, P-Sp- or --
Column 39, line 66-67, reads "one, or more" should read -- one or more --
Column 40, line 16, reads "one of-the" should read -- one of the --
Column 40, line 57, reads "pblymerisable" should read -- polymerisable --
Column 41, line 3, reads "polymerisable-compounds" should read -- polymerisable compounds --

UNITED STATES PATENT AND TRADEMARK OFFICE
CERTIFICATE OF CORRECTION

PATENT NO. : 7,183,418 B2
APPLICATION NO. : 10/928724
DATED : February 27, 2007
INVENTOR(S) : Martin Heeney It is certified that error appears in the above-identified patent and that said Letters Patent is hereby corrected as shown below:

Column 41, line 64, reads "optionally-with" should read -- optionally with --
Column 42, line 9, reads "tag a monomer" should read -- tag ¶a monomer -- (insert a line break)
Column 44, line 23, reads "pblymerisable" should read -- polymerisable --

Signed and Sealed this

Third Day of June, 2008

JON W. DUDAS
*Director of the United States Patent and Trademark Office*